(12) United States Patent
Ros et al.

(10) Patent No.: US 10,271,194 B2
(45) Date of Patent: *Apr. 23, 2019

(54) INCIDENT-CENTRIC MASS NOTIFICATION SYSTEM

(71) Applicant: Siemens Schweiz AG, Zurich (CH)

(72) Inventors: Johannes P. Ros, Bridgewater, NJ (US); Christoph Wienands, Portsmouth, NH (US); Michael Gall, Bridgewater, NJ (US); Christof J. Budnick, Hamilton, NJ (US); Michael Wittemann, Kraichtal (DE)

(73) Assignee: Siemens Schweiz AG, Zurich (CH)

( * ) Notice: Subject to any disclaimer, the term of this patent is extended or adjusted under 35 U.S.C. 154(b) by 0 days.

This patent is subject to a terminal disclaimer.

(21) Appl. No.: 15/472,835

(22) Filed: Mar. 29, 2017

(65) Prior Publication Data

US 2017/0230808 A1 Aug. 10, 2017

Related U.S. Application Data

(63) Continuation of application No. 13/925,829, filed on Jun. 25, 2013, now Pat. No. 9,641,692.

(51) Int. Cl.
| | |
|---|---|
| *G08B 23/00* | (2006.01) |
| *H04W 4/90* | (2018.01) |
| *H04M 11/04* | (2006.01) |
| *H04W 36/00* | (2009.01) |
| *H04M 3/00* | (2006.01) |

(Continued)

(52) U.S. Cl.
CPC .......... *H04W 4/90* (2018.02); *G06F 19/3456* (2013.01); *G08B 21/24* (2013.01); *H04M 3/00* (2013.01); *H04M 3/5116* (2013.01); *H04M 11/04* (2013.01); *H04W 36/00* (2013.01);

(Continued)

(58) Field of Classification Search
CPC ..... H04W 4/22; H04W 76/007; H04W 68/00; H04W 68/005; H04W 68/02; H04W 68/025; H04W 68/04; H04W 68/06; H04W 68/08; H04W 68/10; H04W 68/12; H04W 8/08; G08B 21/24; G06F 19/3456
USPC .............. 340/902, 539.16; 455/404.1, 404.2, 455/412.2, 521, 466, 418; 370/259, 331
See application file for complete search history.

(56) References Cited

U.S. PATENT DOCUMENTS 5,978,720 A * 11/1999 Hieronymus ........ A01D 41/127
340/438
6,215,200 B1 * 4/2001 Genzel ..................... B60Q 1/50
307/10.1

(Continued)

*Primary Examiner* — Hoi C Lau

(57) ABSTRACT

An Incident-centric Mass Notification System ("Incident-centric MNS system") for notifying a plurality of recipients of an Emergency Event is disclosed. The Incident-centric MNS system may include a Mass Notification System ("MNS") Notification Engine, modality corridor ("MoCo") dispatcher, and a plurality of modality corridors, wherein each modality corridor of the plurality of modality corridors establishes, for signal communication, a signal path from a plurality of signal paths, between the MNS Notification Engine and a recipient of the plurality of recipients. The MNS Notification Engine is configured to manage MNS Incidents and Notifications and the MoCo dispatcher is configured to select a first modality corridor from the plurality of modality corridors to establish a first signal path from the MNS Notification Engine.

7 Claims, 19 Drawing Sheets

(51) Int. Cl.
*H04M 3/51* (2006.01)
*G06F 19/00* (2018.01)
*G08B 21/24* (2006.01)

(52) U.S. Cl.
CPC .. *H04M 2201/42* (2013.01); *H04M 2203/205* (2013.01); *H04M 2242/04* (2013.01)

(56) References Cited

U.S. PATENT DOCUMENTS

| | | | | | |
|---|---|---|---|---|---|
| 6,909,407 | B1* | 6/2005 | Schradi | | B60K 35/00 |
| | | | | | 345/156 |
| 6,956,470 | B1* | 10/2005 | Heise | | B60K 35/00 |
| | | | | | 340/438 |
| 7,200,207 | B2* | 4/2007 | Meer | | H04M 3/5116 |
| | | | | | 370/352 |
| 7,391,784 | B1* | 6/2008 | Renkel | | H04L 12/66 |
| | | | | | 370/352 |
| 7,480,501 | B2* | 1/2009 | Petite | | H04M 11/04 |
| | | | | | 340/902 |
| 9,641,692 | B2* | 5/2017 | Ros | | H04M 11/04 |
| 2005/0134443 | A1* | 6/2005 | Hottebart | | G01D 7/02 |
| | | | | | 340/442 |
| 2007/0249372 | A1* | 10/2007 | Gao | | H04L 51/14 |
| | | | | | 455/466 |
| 2009/0040060 | A1* | 2/2009 | Anbuhl | | G01R 31/3682 |
| | | | | | 340/657 |
| 2009/0247113 | A1* | 10/2009 | Sennett | | H04M 11/04 |
| | | | | | 455/404.1 |
| 2010/0142477 | A1* | 6/2010 | Yokota | | H04W 36/0072 |
| | | | | | 370/331 |
| 2012/0081221 | A1* | 4/2012 | Doerr | | B60L 3/0007 |
| | | | | | 340/436 |
| 2012/0239822 | A1* | 9/2012 | Poulson | | H04L 41/0668 |
| | | | | | 709/239 |
| 2012/0284747 | A1* | 11/2012 | Joao | | G06Q 30/02 |
| | | | | | 725/34 |
| 2013/0017846 | A1* | 1/2013 | Schoppe | | G06F 3/0488 |
| | | | | | 455/466 |
| 2014/0376410 | A1* | 12/2014 | Ros | | H04M 11/04 |
| | | | | | 370/259 |
| 2014/0378082 | A1* | 12/2014 | Ros | | H04W 4/22 |
| | | | | | 455/404.1 |

* cited by examiner

INCIDENT-CENTRIC MASS NOTIFICATION SYSTEM

REFERENCE TO RELATED APPLICATIONS

This application is a continuation of and claims the benefit of priority to U.S. patent application Ser. No. 13/925,829, filed Jun. 25, 2013, which is related to U.S. patent application Ser. No. 13/925,833, filed Jun. 25, 2013; both of which are hereby incorporated by reference in their entirety to the extent permitted by law.

BACKGROUND OF THE INVENTION

1. Field of the Invention

The present invention relates to electronic communication systems, and more particularly to electronic events notification systems that are capable of transmitting event-driven messages to various recipients.

2. Related Art

Mass notification systems ("MNS"), herein generally referred to as "MNS Systems," are well known in the art. In general, an MNS System is an attempt at a comprehensive solution that leverages communications technology to not only warn people of danger, but to keep them informed and guide them to safety. MNS Systems may utilize audio, text, and/or multimedia information to provide information and instructions to people who may be impacted by an emergency event. Typically, MNS Systems are utilized for facilities (such as buildings) that have emergency alert and/or security systems. These facilities may be commercial offices, apartments, condominiums, government buildings, schools, campus of buildings, etc. Generally the MNS Systems are integrated into the emergency alert and/or security systems. As an example, in an emergency event such as a fire, severe weather, a school shooting, or an act of terrorism, people within the facilities and other people, such as, for example, first responders or family members, of the people within the facilities, may be notified of the situation.

Examples of known MNS Systems include facility emergency monitoring systems such as generic alarm systems or fire alarms that include, for example, bells, horns, lights, and/or sirens capable of directing occupants of the facility to evacuate the area. Additionally, these MNS Systems may send emergency notifications to the appropriate first responders, such as, for example, the police or fire department, to managers and/or other responsible personnel of the facility, or to other interested people, such as, for example, parents of children attending a school.

Examples of known MNS Systems are described in: U.S. Pat. No. 8,243,887, titled "Identification of Notifications In a Mass Notification System," which issued to Conahan on Aug. 14, 2012; U.S. Pat. No. 7,277,018, titled "Computer-enabled Networked, Facility Emergency Notification, Management and Alarm System," which issued to Reyes et al. on Oct. 2, 2007; U.S. Pat. No. 7,724,130, titled "Systems and Methods For Distributing Emergency Messages," issued to Norstrom et al., on May 25, 2010; and U.S. Pat. No. 8,384,549, titled "Event Communication System For Forwarding User Alerts," issued to Lemmon, all of which are herein incorporated by reference in their entirety.

Turning to FIG. 1, a block diagram of an example of an implementation of a MNS system 100 in signal communication with a facility network 102, via signal path 104, is shown. The facility network 102 may be an internal network within a given building or a campus with multiple buildings. The facility network 102 may include a computer network such as an enterprise private network, local area network ("LAN"), wide area network ("WAN"), and campus area network ("CAN"). The facility network 102 may be in signal communication with a building management system 106, fire protection system 108, security system 110, telecommunication system 112, perimeter Internet access system 114, a common alerting protocol ("CAP") request system 116, other emergency devices 118 that provide emergency inputs, and emergency alert system 120, via signal paths 122, 124, 126, 128, 130, 132, 134 and 136, respectively. The telecommunication system 112 may include any type of telecommunication network that includes a private branch exchange ("PBX") or other telephone exchange that connects to a public switched telephone network ("PSTN"). The telecommunication system 112 may also include devices capable of communicating via a wireless cellular communication network, microwave communication network, and/or satellite communication network (collectively shown as communication network 138). Similarly, the Internet access system 114 may include devices (such as servers and firewalls) that define a physical or logical sub-network that contains and exposes external-facing services of the facility network 102 to a larger untrusted network such as the Internet 140. Unlike the telecommunication system 112 and Internet access system 114, the emergency alert system 120 may be more generic alarm notification systems, such as, for example, a system of bells, horns, lights, loudspeakers, and/or sirens capable of notifying occupants of the facility of the emergency. Ultimately, the telecommunication system 112, Internet access system 114, and emergency Alert system 120 allow communicating with target recipients 142 of the MNS system 100 in the case of an emergency. The target recipients 142 may include the occupants of the facility, first responders, people outside of the facility within a specific distance, or other interested people.

Unfortunately, known MNS systems 100 are limited in: the type of messages and/or notifications that they may generate; the manner in which they communicate those messages and/or notifications; the consistency and completeness of the notifications and/or messages; and flexibility of the information provided in the notifications and/or messages. As such, there is a need for a new and improved MNS system that overcomes these problems.

SUMMARY

In order to solve the previously discussed problems with known MNS systems, disclosed is an Incident-centric Mass Notification System ("Incident-centric MNS system") for notifying a plurality of recipients of an Emergency Event, where the Emergency Event may be any Event that may cause significant disruption to people, including damage, injuries, or deaths. The Incident-centric MNS system may include a Mass Notification System ("MNS") Notification Engine, modality corridor ("MoCo") dispatcher, and a plurality of modality corridors, wherein each modality corridor of the plurality of modality corridors establishes, for signal communication, a signal path from a plurality of signal paths, between the MNS Notification Engine and a recipient of the plurality of recipients. The MNS Notification Engine is configured to manage MNS Incidents and Notifications and the MoCo dispatcher is configured to select a first modality corridor from the plurality of modality corridors to establish a first signal path from the MNS Notification Engine.

Additionally disclosed is a MNS Notification Engine for use in the Incident-centric MNS system. The MNS Notification Engine may include logic configured to manage a plurality of MNS Incidents and a plurality of Notifications and a user interface ("UI") that allows an MNS User (e.g., a System User or recipient user of the Incident-centric MNS system) to interface with the MNS Notification Engine.

Other systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims.

BRIEF DESCRIPTION OF THE DRAWINGS

The invention can be better understood by referring to the following figures. The components in the figures are not necessarily to scale, emphasis instead being placed upon illustrating the principles of the invention. In the figures, like reference numerals designate corresponding parts throughout the different views.

DETAILED DESCRIPTION OF THE INVENTION

In order to solve the previously discussed problems with known MNS systems, disclosed is an Incident-centric Mass Notification System ("Incident-centric MNS system") for notifying a plurality of recipients of an Emergency Event, where the Emergency Event may be any Event that may cause significant disruption to people, including damage, injuries, or deaths. The Incident-centric MNS system may include a Mass Notification System ("MNS") Notification Engine, modality corridor ("MoCo") dispatcher, and a plurality of modality corridors, wherein each modality corridor of the plurality of modality corridors establishes, for signal communication, a signal path from a plurality of signal paths, between the MNS Notification Engine and a recipient of the plurality of recipients. The MNS Notification Engine is configured to manage MNS Incidents and Notifications and the MoCo dispatcher is configured to select a first modality corridor from the plurality of modality corridors to establish a first signal path from the MNS Notification Engine.

As further described in detail herein, the Notification Engine of the Incident-centric MNS system may include logic configured to manage a plurality of MNS Incidents and a plurality of Notifications associated with such MNS Incidents and a user interface ("UI") that allows an MNS user to interface with the MNS Notification Engine.

Figure 1:
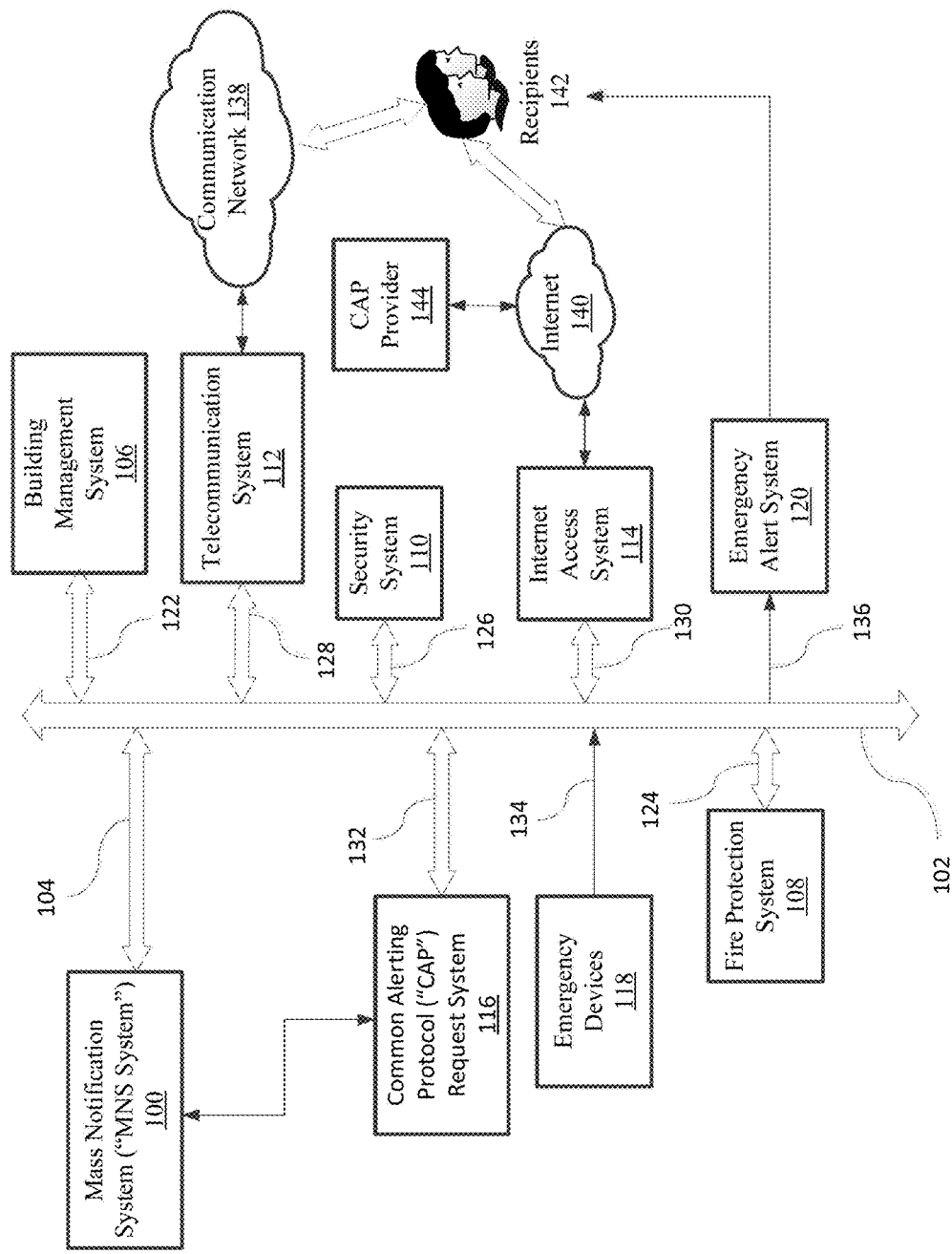
FIG. 1 is a block diagram of an example of an implementation of a known Mass Notification System ("MNS") in signal communication with a facility network.
Figure 2:
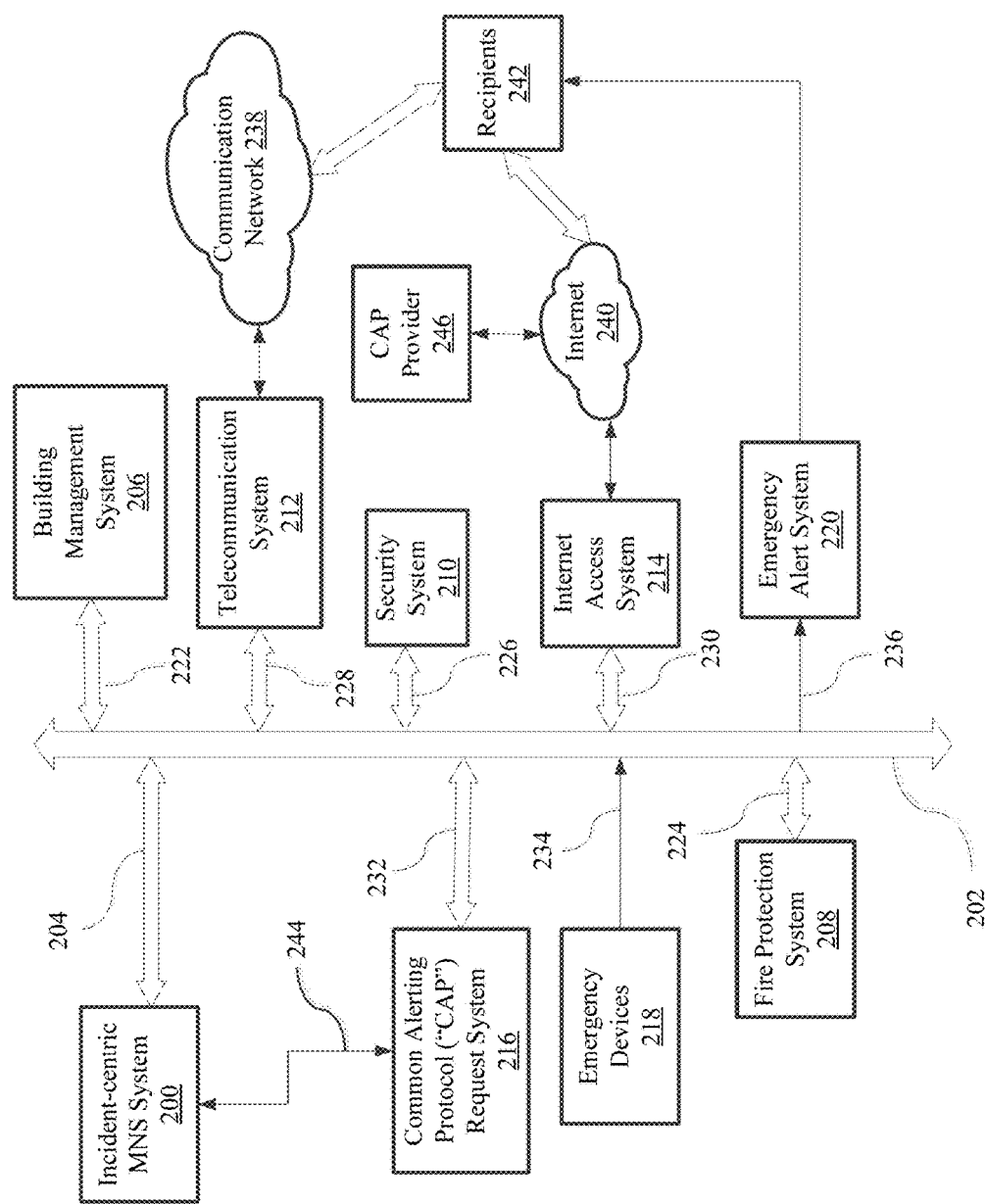
FIG. 2 is a block diagram of an example of an implementation of an Incident-centric Mass Notification System ("Incident-centric MNS system") in signal communication with a facility network in accordance with the invention.

In FIG. 2, a block diagram of an example of an implementation of an Incident-centric MNS system 200 in signal communication with a facility network 202, via signal path 204, is shown. Similar to FIG. 1, the facility network 202 may be an internal network within a given building, a campus with multiple buildings, or a geographic region with multiple campuses with multiple buildings. The facility network 202 may include a computer network such as an enterprise private network, local area network ("LAN"), wide area network ("WAN"), and campus area network ("CAN"). In this example, the facility network 202 may include corporate private network and a control room network. The facility network 202 may be in signal communication with a building management system (also known as a building automation system) 206, fire protection system 208, security system 210, telecommunication system 212, perimeter Internet Access System 214, a common alerting protocol ("CAP") request system 216, other emergency devices 218 that provide emergency inputs, and emergency alert system 220, via signal paths 222, 224, 226, 228, 230, 232, 234 and 236, respectively.

The telecommunication system 212 may include any type of telecommunication network that includes a private branch exchange ("PBX") or other telephone exchange that connects to a public switched telephone network ("PSTN"). The telecommunication system 212 may also include devices capable of communicating via a wireless cellular communication network, microwave communication network, and/or satellite communication network (collectively shown as communication network 238). Similarly, the Internet Access System 214 may include devices (such as servers and firewalls) that define a physical or logical sub-network that contains and exposes external-facing services of the facility network 202 to a larger untrusted network such as the Internet 240. Unlike the telecommunication system 212 and Internet Access System 214, the emergency alert system 220 may be a more generic alarm notification systems, such as, for example, a system of bells, horns, lights, visual displays, loudspeakers, and/or sirens capable of notifying occupants of the facility of the emergency. Ultimately, the telecommunication system 212, Internet Access System 214, and emergency alert system 220 allows communicating with recipients 242 of the Incident-centric MNS system 200 in the case of an emergency (i.e., an Emergency Event).

The CAP request system 216 may be in signal communication with the Incident-centric MNS system 200 via signal path 244. The CAP request system 216 is a system that is capable of receiving CAP information from a CAP provider 246 that is located remote from the facility via the Internet 240. The CAP request system 216 may then provide that information to the Incident-centric MNS system 200 via either signal path 244 or via signal paths 204 and 232 and facility network 202. Examples of CAP providers 246 include, for example, the Department of Homeland Security, Department of the Interior's United States Geological Survey, Department of Commerce's National Oceanic and Atmospheric Administration ("NOAA"), National Weather Service, California Office of Emergency Services, and other state and local government agencies.

In this example, the recipients 242 may be system end-device, recipient users (i.e., individuals and indirectly their recipient user end-devices), recipient groups, or recipient locations. A system end-device (also referred to as a system output device or recipient device) may be a non-personal, public communication device that receives Notifications from Incident-centric MNS system 200 and relays the Notification to recipient users. The system end-device may be a system managed device, which is supervised by the Incident-centric MNS system 200. Examples of a system end-device may include a visual display (such as display monitor, lighted sign, lighted emitting diode ("LED") signs, etc.), media displays (e.g., LCD television), universal resource locators ("URLs") for NOAA CAP RSS feeds, panic buttons, audio devices, emergency hotline, fire alarm control panel, loudspeakers, bells, sirens, Line-level Audio ("LLA") devices, web pages, social media accounts (e.g., Twitter®, Facebook®), etc. A system end-device may have one or more MNS End-Points, where each such end-point is addressable via its MNS End-Point address and may support multiple types of notification content.

A recipient user end-device (also generally referred to as recipient user output device) is a personal device associated with a recipient user, such as, for example, a telephone, computer, mobile device such as a mobile computer, mobile telephone, tablet, PDA device, pager, etc. The recipient user end-device may also be email addresses/boxes and desktop notification on various types of computing devices. The recipient user end-device is a device capable of receiving outbound Notifications from the Incident-centric MNS system 200 and present them to a recipient user associated with the recipient user end-device. The recipient user end-device may also allow the sending of inbound Notifications by the recipient user (acting as a source of an Emergency Event (not shown)) to the Incident-centric MNS system 200. A recipient user end-device may have one or more MNS End-Points, where each such end-point is addressable via its MNS End-Point Address and may supports multiple types of notification content.

The recipient users may include the occupants of the facility, first responders (such as, for example, police, fire department, paramedics, etc.), people outside of the facility within a specific distance, or other interested people. A recipient user is generally an individual who is a: (1) recipient because the Incident-centric MNS system 200 may address Notification to him/her and (2) a MNS user because he/she may be able to interact with the Incident-centric MNS system 200 when receiving Notifications (i.e., Outbound Notifications) or when generating and sending Inbound Notifications to the Incident-centric MNS system 200.

A recipient group is a type of recipient 242 that includes one or more recipients 242, such as a group of system end-devices 324, recipient user end-devices 326, recipient users 328 associated with respective recipient user end-devices 326, recipient locations, other recipient groups or a combination thereof. Additionally, a recipient location is a grouping mechanism in the Incident-centric MNS system 200 that is used to group and manage together recipient users, system end-devices, recipient groups, and other recipient sub-locations that are present at certain physical locations. In general, both a recipient group and recipient location are a Composite Recipients containing one or more "Simple" Recipients (i.e., an individual recipient). Additionally, a recipient group may include one or more recipient locations and, similarly, a recipient location may include one or more recipient groups.

The building management system 206 may be able to control various building environment and safety devices, such as lights, thermostats in heating, ventilation, and air conditioning ("HVAC") systems, refrigeration systems, meters, and alarm systems (such as, for example, fire protection system 208, security system 210 and emergency alert system 220) at the facility. Communication with these automation systems over the facility network 202 may occur over one or more networks, such as BACnet® or with other types of building automation gateways, such as an Desigo® gateway commercially available from Siemens Building Technologies Division of Siemens Schweiz AG, of Zug, Switzerland. The networks may be dedicated automation system networks or shared voice/data networks wired and/or wireless, such as IEEE 802.3 or token ring networks. The fire protection system 208 may be any automated fire detection and reporting system that may include subsystems, such as, for example, a FireFinder™ XLSV system produced by Building Technologies Division of Siemens Industry, Inc. of Florham Park, N.J. The security system 210 may be any building security system, such as, for example, building security systems with Siveillance™ commercially available from Siemens Building Technologies Division of Siemens Schweiz AG, of Zug, Switzerland. Moreover, the CAP request system 216 is any system capable of receiving public warnings using CAP based data. It is appreciated by those skilled in the art that CAP warnings are provided by many government agencies and companies. The emergency devices 218 may be standard known "dry contact" and/or digital input devices, such as, for example, a fire alarm button and/or lever (generally known as a "fire pull station") or other emergency switch that may be activated by a person within the facility in the case of an emergency.

It is appreciated by those skilled in the art that the circuits, components, modules, and/or devices of, or associated with, the Incident-centric MNS system 200 are described as being in signal communication with each other, where signal communication refers to any type of communication and/or connection between the circuits, components, modules, and/or devices that allows a circuit, component, module, and/or device to pass and/or receive signals and/or information from another circuit, component, module, and/or device. The communication and/or connection may be along any signal path between the circuits, components, modules, and/or devices that allows signals and/or information to pass from one circuit, component, module, and/or device to another and includes wireless or wired signal paths. The signal paths may be physical, such as, for example, conductive wires, electromagnetic wave guides, cables, attached and/or electromagnetic or mechanically coupled terminals, semi-conductive or dielectric materials or devices, or other similar physical connections or couplings. Additionally, signal paths may be non-physical such as free-space (in the case of electromagnetic propagation) or information paths through digital components where communication information is passed from one circuit, component, module, and/or device to another in varying digital formats without passing through a direct electromagnetic connection.

Figure 3:
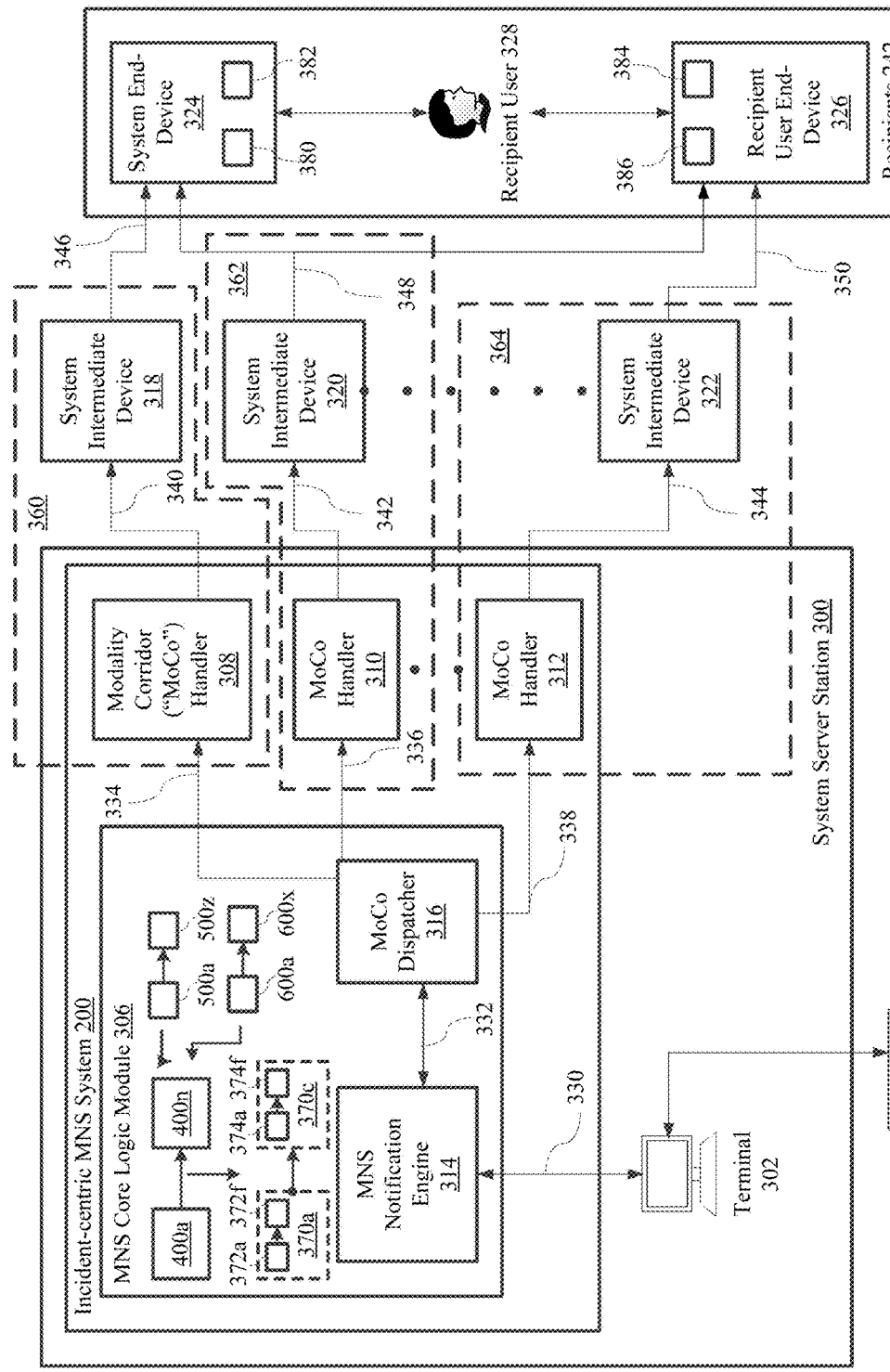
FIG. 3 is a block diagram of an example of an implementation of the Incident-centric MNS System shown in FIG. 2 in accordance with the invention.

Turning to FIG. 3, shown is a block diagram of an example of an implementation of the Incident-centric MNS System 200 shown in FIG. 2. The Incident-centric MNS System 200 may be part of a system server station 300 and in signal communication with a terminal 302. The terminal 302 may be a system server screen (such as, a computer monitor) that allows a MNS user (such as System User 304) to interface with the system server station 300 via a user interface ("UI") 305. In general the Incident-centric MNS system 200 is an improved MNS system that includes a collection of hardware and/or software computing nodes running associated software for providing MNS functionality as described herein to MNS Users (both System User 304 and possibly a recipient user) and logic configured to manage a plurality of MNS Incidents 370a-370c and a plurality of Notifications 372a-372f, 374a-374f associated with such MNS Incidents 370a-370c and a UI that allows the MNS user to interface with the MNS Notification Engine 314.

The Incident-centric MNS System 200 may include a MNS core logic module 306 and a plurality of MoCo handlers 308, 310, and 312, respectively. The MNS core logic module 306 may include a MNS Notification Engine 314 and MoCo dispatcher 316. In general, the system server station 300 may be in signal communication with a plurality of system intermediate devices (318, 320, and 322) that may be in signal communication with a system end-device 324 and recipient user end-device 326. Both the system end-device 324 and recipient user end-device 326 may be in communication with a recipient user 328. As an example, if the system end-device 324 is a visual display or an audio producing device, the system end-device 324 will communicate with the recipient user 328 by transmitting outbound Notifications of the Emergency Event in the form of visual and/or audio information that the recipient user 328 can see and hear.

The MNS Notification Engine 314 may include logic configured to manage a plurality of MNS Incidents 370a-370c and a plurality of Notifications 372a-372f, 374a-374f associated with such MNS Incidents 370a-370c and a UI 305 that allows an MNS user to interface with the MNS Notification Engine. In this example, the MNS user may be either the System User 304 or the recipient user 328. In the case of the System User 304, the System User 304 may be a System Operator, System Administrator, or Customer Service Representative. The System Operator may be a trained System User for operating the Incident-centric MNS System 200 during an Emergency Event, including initiating and managing MNS Incidents. A System Administrator may be a trained System User for administrating the Incident-centric MNS System 200 in preparation for an Emergency Event, including engineering and/or configuring Incident Templates 400a-400n, Notification Templates 500a-500z and 600a-600x, MNS End-Devices (such as, for example, system end-device 324 and recipient user end-device 326), and Recipients 242. The Customer Service Representative may be a trained customer-facing MNS User who performs privileged installation, engineering, and configuration tasks on the Incident-centric MNS System 200 on behalf of the customer that is utilizing the Incident-centric MNS System 200.

In this example, the terminal 302 may be in signal communication with the MNS Notification Engine 314 via signal path 330. The MoCo dispatcher 316 may be in signal communication with the MNS Notification Engine 314, first MoCo handler 308, second MoCo handler 310, and third MoCo handler 312 via signal paths 332, 334, 336, and 338, respectively. The first MoCo handler 308 may be in signal communication with first system intermediate device 318, the second MoCo handler 310 may be in signal communication with the second system intermediate device 320, and the third MoCo handler 312 may be in signal communication with the third system intermediate device 322 via signal paths 340, 342, and 344, respectively. The system end-device 324 may be in signal communication with both the first system intermediate device 318 and second system intermediate device 320 via signal paths 346 and 348, respectively. Moreover, the recipient user end-device 326 may be in signal communication with the second system intermediate device 320 and third intermediate device 322 via signal paths 348 and 350, respectively.

It is appreciated that while only three MoCo handlers 308, 310, and 312 and three system intermediate devices 318, 320, and 322 are shown in this example, there could be additional MoCo handlers with corresponding system intermediate devices without departing from the spirit of the invention. Additionally, there may also be multiple intermediate devices (which may include software modules) per individual MoCo handler. In general, the MoCo dispatcher 316 functions by selecting the appropriate MoCo handler 308, 310, or 312 for sending outbound Notifications.

In this example, the MNS Notification Engine 314 may include a collection of software and/or hardware modules for managing MNS Incidents 370a-370c and associated Notifications 372a-372f, 374a-374f. The MNS Notification Engine 314 may include the core business logic of the Incident-centric MNS System 200 including the capability of sending outbound Notifications. The System User 304 may interface with the MNS Notification Engine 314 via the terminal 302 utilizing the UI 305. As mentioned earlier, the System User 304 is a person who interacts with Incident-centric MNS System 200 via MNS commands, primarily in the capacity of a System Operator, system administrator, or Customer Service Representative via the UI 305 on the terminal 302. However, a MNS User 304 that is not a System User may include a client user such as the recipient user 328.

Expanding on this, the type of MNS User 304 may be divided into two classes based on their user interface access. Customer Service Representatives and System Users may access the system server station 300 via, for example, the UI 305, a general management system ("GMS") platform UI, such as, for example, Desigo CC™ (from Siemens Building Technologies Division of Siemens Schweiz AG, of Zug, Switzerland), web-based UI, and telephone voice menu, where the GMS platform is a brand-neutral general management station platform that has the capability of hosting extension modules such as the Incident-centric MNS system 200. On the other hand, the client users, in this example, may only access the system server station 300 via a web-based UI that may be similar to the UI 305 but with limited capabilities.

In this example, an MNS Incident 370a-370c (also referenced herein as an "Incident object") is an structured object in the Incident-centric MNS System 200 instantiated by the MNS Notification Engine 314 and utilized by a System Operator (such as the System User 304) to manage and keep track of the Emergency Event. An MNS Incident or Incident object (e.g., 370a or 370c in FIG. 3) is instantiated by the MNS Notification Engine 314 to have functionality and elements based on Incident Templates 400a-400n specified by a System User 304 for association with an Emergency Event as further described herein. Such Incident Templates 400a-400n are generated by the MNS Notification Engine 314 from Notification Templates 500a-500z and 600a-600x as directed by a System User 304. Again, an Emergency Event is any Event that may cause significant disruptions to people, including damage, injuries, or deaths. Examples of Emergency Events include fire, hazardous materials spill, flood or flash flood, hurricane, tornado, winter storm, earthquake, communications failure, radiological accident, civil disturbance, explosion, etc. Generally, an Event is a situation that a System Operator either needs to be aware of, or needs to respond to.

Notifications 372a-372f, 374a-374f that are generated by the MNS Notification Engine 314 (also known as outbound Notifications) keep recipients 242 informed during Emergency Events. Generally, the Incident-centric MNS System 200 sends Notifications via MNS End-Devices (such as, for example, system end-device 324 and recipient user end-device 326) and there are typically two types of Notifications, which are Messages and Live Announcements. A Message is a type of Notification that can be sent to recipients 242 during an MNS Incident. The pre-configured details of Messages are stored in Message Templates 500a-500z, where a Message Template is a type of Notification Template for the purpose of holding the pre-configured details of a Message. In this example, a Message Template is an object structure for holding the Notification's pre-configured Control Options, Scheduler settings, recipients 242, and Content: TEXT, AUDIO, and MULTIMEDIA. Notification Template objects are defined and organized in Notification Template Hierarchies, and can be copied into Incident Templates 400a-400n for use within MNS Incidents 370a-370c. A Notification Template Hierarchy is a folder structure for holding Notification Templates. There are two types of Notification Templates, which are Message Templates 500a-500z and Live Announcement Templates 600a-600x. Additionally, Message templates may be repeatedly launched as Messages (e.g., 372a and 374a) by the MNS Notification Engine 314 in accordance with a corresponding MNS Incident 370a or 370c as managed by the MNS Notification Engine.

A Live Announcement (e.g., 372b of MNS Incident 370a) is a type of Notification where a real time audio stream from the System Operator is delivered to recipients 242 during the MNS Incident associated with the Live Announcement. Pre-configured details of Live Announcements are stored in Live Announcement Templates 600a-600x, where a Live Announcement Template is a type of Notification Template for the purpose of holding the pre-configured details of a Live Announcement. In this example, a Live Announcement template 600a-600x allows for the configuration of, for example, the following: general settings that includes a name, description, and extended description of the live announcement; a priority of the Live Announcement; a Live Announcement source, and recipients 242, with limitations on delivery. As an example, if the recipients 242 are system end-devices, the Live Announcement may be sent only to the audio-enabled devices such as loudspeakers; if the recipients 242 are recipient groups, the Live Announcement may be sent to only the audio-enabled devices within those groups; and if the recipients 242 are recipients locations, the Live Announcement may be sent only to the audio-enabled devices within those locations. Additionally, Live Announcement templates may be repeatedly launched by the MNS Notification Engine 314 as Live Announcements (e.g., 372b) associated with a respective MNS Incident (e.g., 370a).

In this example, a Triggering incident is the automatic initiation of incidents based on inbound Notifications, where inbound Notifications are received by the Incident-centric MNS System 200 from sources, such as, for example, fire panels, CAP RSS feeds, or recipient users, via MNS End-Devices (not shown) for the purpose of raising Events and triggering MNS Incidents. Through the UI 305, the System User 304 may specify the rules that describe the conditions for when the trigger shall occur. In this example, the UI 305 and associated mechanism for triggering the initiation of MNS Incidents may be called an Easy Trigger.

In this example, the term Notifications is used to refer to three different stages of notification and notification template specifically: Notification Templates (e.g., 500a and 500z) that exist in the notification template hierarchy (e.g., 500a-500z); Notification Templates (e.g., 372a-372f) that exists within an MNS Incident (e.g., 370a) or within a launch group of that MNS Incident; and messages and live announcements which are launched by the MNS Notification Engine 314 to and received by recipients. The Notification Templates that exist in the notification template hierarchy are used by the MNS Notification Engine to populate MNS Incident Templates 400a-400n as directed by a System User 304 using the UI 305. Some of these Notification Templates (e.g., certain ones of the Message Templates 500a-500z) may be pre-defined and provided to a customer organization, such as business, university campus, and hospital, utilizing the Incident-centric MNS System 200 where these pre-defined Notification Templates may include typical and common sets of notification that customer organizations might need during an Emergency Event. Other more tailored Notification Templates may be added later to the Notification Template Hierarchy 500a-500z and 600a-600x by the business because the Notification Templates in the Notification Template Hierarchy are customizable to varying degrees. In general, all the Notifications sent to recipients 242 are based off a Notification Template that originates in the Notification Template Hierarchy.

The Notification Templates that exist within an Incident Template or within a launch group of that Incident Template are based on templates from the Notification Template Hierarchy (i.e., collectively 500a-500z and 600a-600x). They may be more customized for the specific incident than the template in the hierarchy, where Message Templates may contain user variables, system variables, or event variables.

In this example and as further explained below, within an Incident Template (e.g., 400a), a Launch Group is a set of related Notification Templates for the purpose of launching the corresponding Notifications (e.g., 372a-372f) at the same time during the various stages of an MNS Incident (e.g., 370a), where the Incident Templates may contain multiple Launch Groups. As an example, the designated START Launch Group (e.g., Launch Group "LG1" 404 in FIG. 4) contains the templates for Notifications that the MNS Notification Engine 314 recognizes as needing to be launched when the respective MNS Incident 370a is initiated based on a corresponding Emergency Event. Other Launch Groups as depicted in FIG. 4 may contain, for example, Notification Templates that specify an all clear Message or a Live Announcement.

Returning to the MNS core logic module 306, the MoCo dispatcher 316 may be a hardware and/or software module that is responsible for selecting a MoCo handler 308, 310, or 312 based on a Notification (e.g., 372a) it has received from the MNS Notification Engine 314 for delivering to an MNS End-Point Address where the MNS End-Point Address is the address of an MNS End-Point (e.g., 380, 382, 384 or 386), which supports one or more Notification Content Types as further described herein. In this example, each combination of MNS End-Point Address and Notification Content Type is mapped onto an MNS Modality. In this case, an MNS End-Point 380, 382, 384 or 386 is an addressable termination point for the Incident-centric MNS System 200 within an MNS End-Device. Each MNS End-Device contains one or more MNS End-Points 380, 382, 384 or 386. An MNS End-Point acts as the address target for outbound Notifications, and as the address source for inbound Notifications. Each MNS End-Point has one and only one MNS End-Point Address, which supports one or more Notification Content Types. Any valid combination of MNS End-Point Address and Notification Content Type maps onto one or more MNS Modalities.

Figure 4:
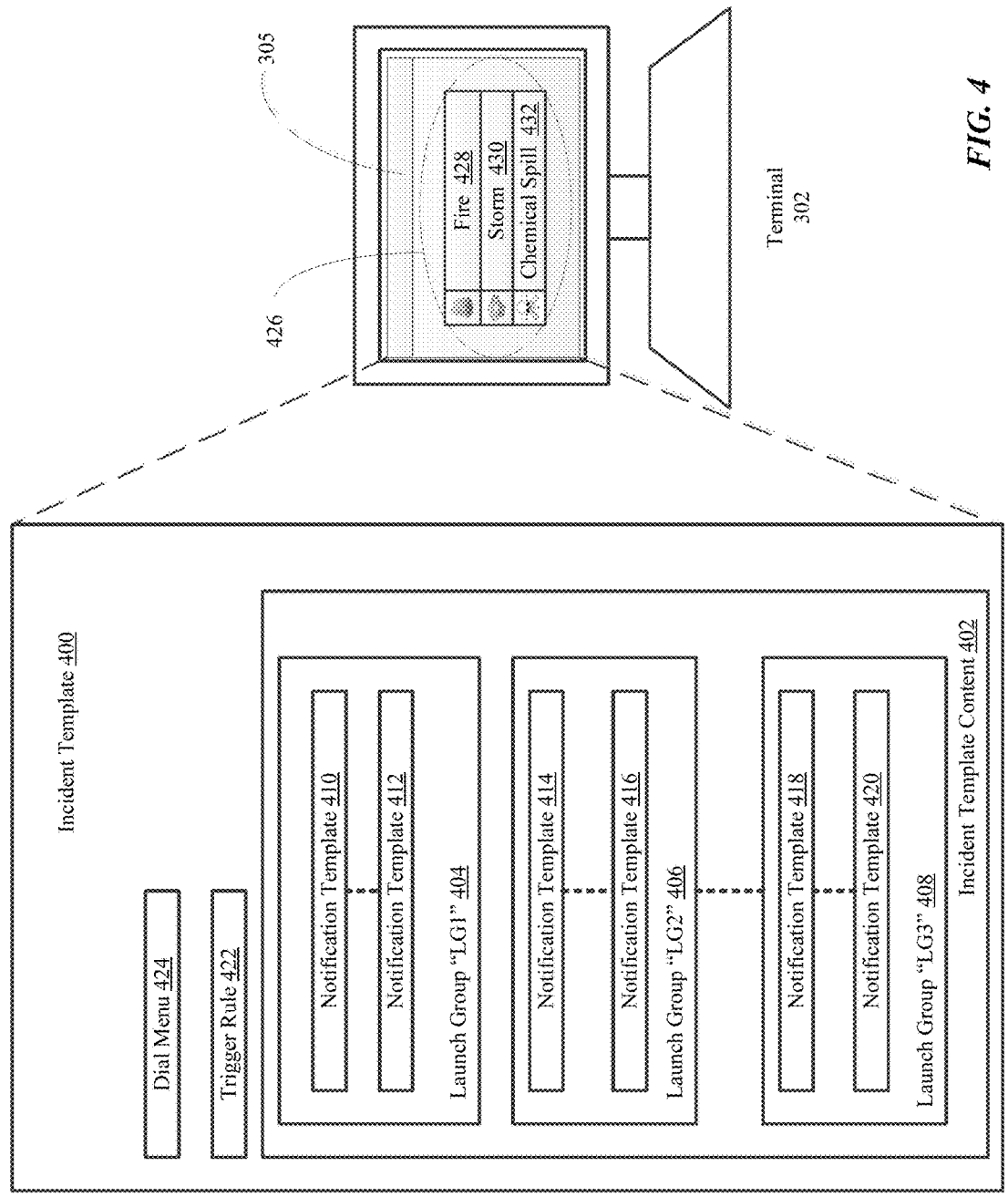
FIG. 4 is a block diagram of example of an implementation of an Incident Template in accordance with the invention.

In FIG. 4, a block diagram of example of an implementation of an Incident Template 400 is shown that identifies the structural elements for Incident Templates 400a-400n used by the MNS Notification Engine 314 to generate and manage Incident objects or MNS Incidents 370a-370c in response to a triggering Event. The Incident Template 400 is an object structure for holding the MNS Incident's pre-configuration Notification Templates. These pre-configured Notification Templates are organized within the Incident Template Content 402 includes at least one launch group which may be known as a START launch group ("LG1") 404. In this example, three launch groups LG1 404, LG2 406, and LG3 408 are shown. It is appreciated that additional launch groups may also be included but for illustrative purposes only three are shown in this example. In this example, LG1 404 may be the designated START Launch Group that includes Notification Templates 410 through 412 that will be launched when an MNS Incident 370a-370c is initiated or instantiated by the MNS Notification Engine 314. LG2 406 may be the update Launch Group that includes Notification Templates 414 through 416 that will be launched during the course of the corresponding MNS Incident (e.g., 370a) in response to the initial Emergency Event, at the discretion of the System Operator 304, to provide further updates to the Recipients 242. LG3 408 may be the designated CLEAR-ALL Launch Group that will be launched when the System Operator 304 has started to close the Incident, resulting in all active Notifications (e.g., 372a) within this Incident object (e.g., 370a) to reach the state of Canceled or Expired, after which the Incident object will reach the state Closed.

The Incident Template 400 may also include a Trigger Rule 422 that the System Operator may create and modify via the UI. The Trigger Rule 422 describes the conditions for which a Trigger Incident shall occur, where the Trigger Incident is an automatic initiation of MNS Incidents or Incident objects by the MNS Notification Engine 314 based on an inbound notification to the Incident-centric MNS System 200. These Trigger Incidents may be configured to require human interaction to confirm the initiation of an automatically Triggered Incident. The Incident Template 400 may also include a dial menu 424 that is a dial-in feature that may be utilized by the System Operator 304 to easily and quickly cause the MNS Notification Engine 314 to initiate MNS Incidents and launch related Notifications via a telephone.

The Incident Template 400 may be simplified into quick launch graphical pictograms 426 on the UI 305 of terminal 302 that represent different types of Emergency Events for which the System Operator 304 may quickly need to initiate MNS Incidents and launch related Notifications. In this example, the first pictogram 428 may appear on the UI 305 as an "Easy Button" or "Easy Trigger" representing a fire. The second pictogram 430 may appear on the UI 305 as an "Easy Button" or "Easy Trigger" representing a storm. Finally, the third pictogram 432 may appear on the UI 305 as an "Easy Button" or "Easy Trigger" representing a chemical spill. It is appreciated that while only three "Easy Buttons" or "Easy Triggers" are shown in this example, there could be additional "Easy Buttons" or "Easy Triggers" without departing from the spirit of the invention.

Figure 5:
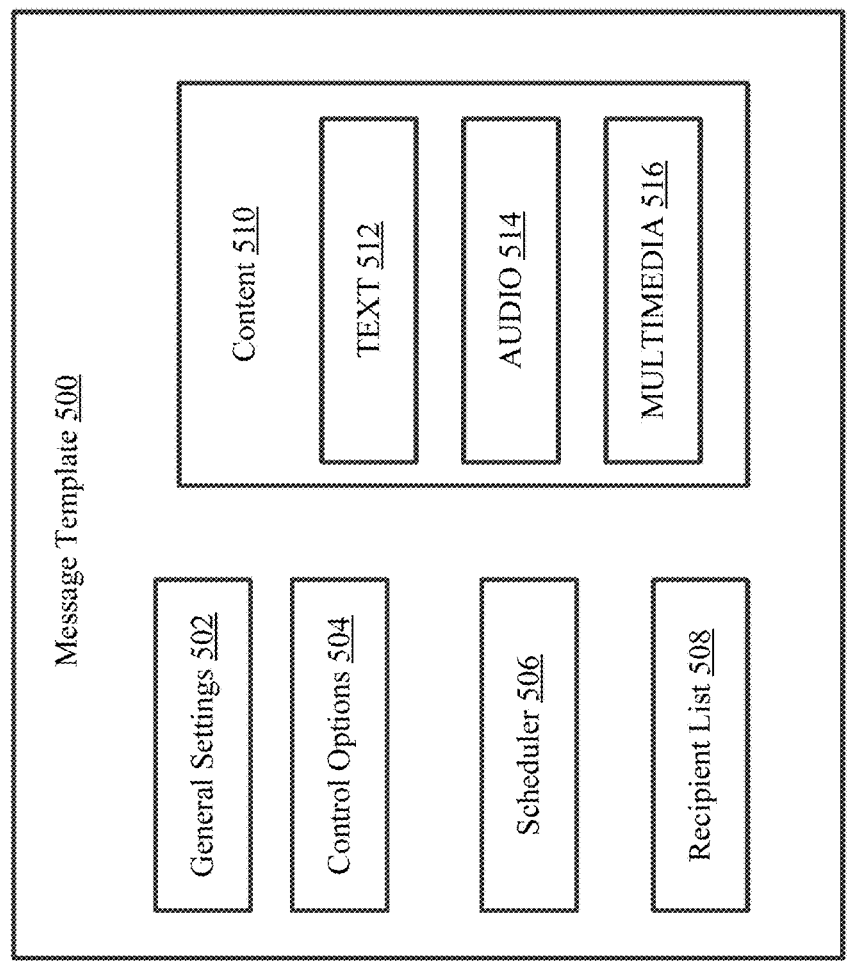
FIG. 5 is a block diagram of an example on an implementation of a Message Template based on the Incident Template shown in FIG. 4 in accordance with the invention.

Turning to FIG. 5, a block diagram of an example on an implementation of a Message Template 500 is shown that identifies the structural elements for Message Templates 500a-500z used by the MNS Notification Engine 314 to generate Incident Templates 400a-400n and subsequent MNS Incidents 370a-370c in response to a triggering Event. The Message Template 500 may be one of the Notification Templates 410, 412, 414, 416, 418, or 420 shown in FIG. 4. In this example, the Message Template 500 may include logic that includes data structure (also known as object structure) configured to hold pre-configured details about the Message. The Message is a type of Notification that can be sent to recipients 242 during an MNS Incident. The pre-configured details of the Message are stored in the Message Template 500. In this example, the Message Template 500 is an object structure for holding the Notification's pre-configured General Settings 502, Control Options 504, Scheduler settings 506, recipients list 508, and Content 510. The Content 510 may include: TEXT 512, AUDIO 514, and MULTIMEDIA 516. In this example, the Message Content 510 may include text content, which may include three types of Message text variables which are system variables, user variables, and event variables. The Message text variables are placeholders in the text content 512 of the Message Template 500 whose values may be assigned when a Message is launched from the Message Template 500. The Message text variables may be supplied by the System User or automatically by the MNS core logic module 306. The Content 510 may also include audio content or multimedia content. These Message Template 500 objects are defined and organized in Notification Template Hierarchies (collectively represented as 500a-500z in FIG. 3), and can be copied into Incident Templates 400a-400n by the MNS Notification Engine 314 for use in generating and managing the corresponding MNS Incidents 370a-370c. In this example, a Notification Template Hierarchy is a folder structure for holding Notification Templates.

In this example, the Message Template 500 allows for the configuration of the object structure by the System Operator 304. The General Settings 502 may include information, such as, for example, the name, description, extended description of the Message, and description of the Message type. The Control Options 504 may be used by the MNS Notification Engine and MoCo Dispatcher to control the priority of the Message, the Message priority tolerance, Message expiration, and Message escalation. The Message priority tolerance governs which Messages can play simultaneously on a device so as to control what priorities other Messages need to have to allow concurrent displaying and/or playing. The Message Expiration specifies the end of the Message's life, at which point the MNS Notification Engine 314 will cause the Message to be removed from all MNS End-Devices displaying or playing the Message. The Message escalation determines deliveries to alternative recipient user devices of the same, or another, recipient user when earlier delivery attempts to that recipient user have failed.

The Message Scheduler 506 may identify the schedule for the time of delivery of the Message. This Message Scheduler 506 may be configured, for example, to cause the MNS Notification Engine 314 to postpone the delivery of the Message to a later date and/or time and to schedule repeated delivery of the message. The recipient list 508 may include rules as to which recipients 242 receive the Message.

Figure 6:
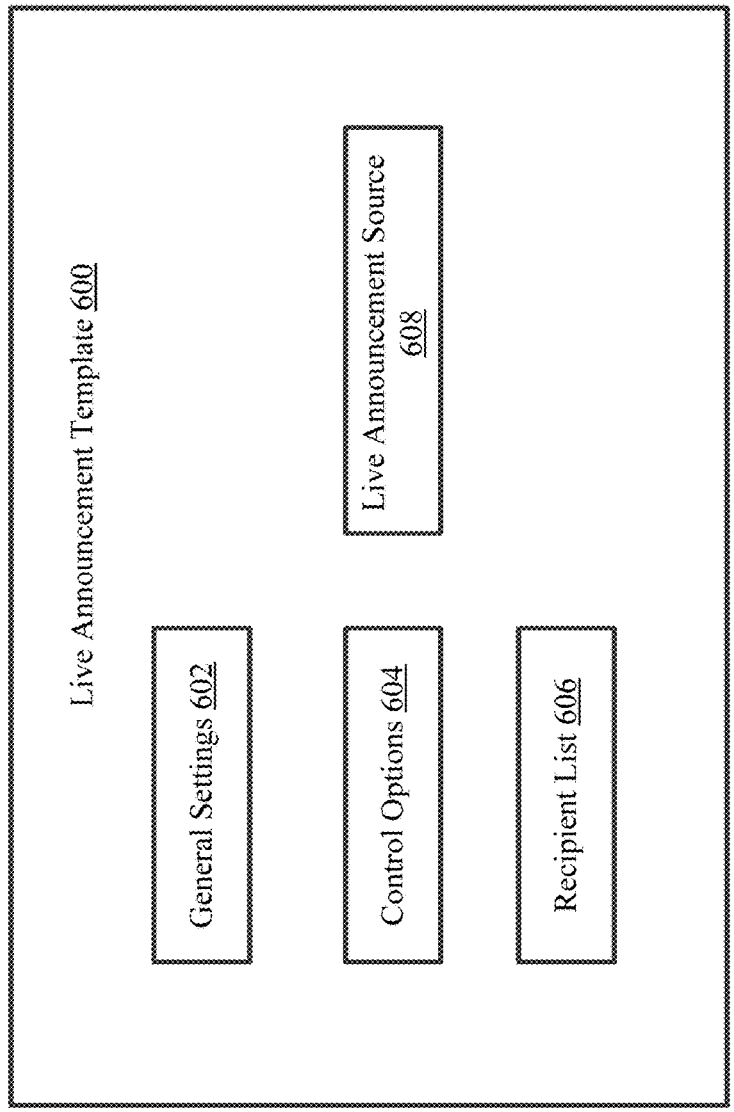
FIG. 6 is a block diagram of an example on an implementation of a Live Announcement Template based on the Incident Template shown in FIG. 4 in accordance with the invention.

In FIG. 6, a block diagram of an example on an implementation of a Live Announcement Template 600 is shown that identifies the structural elements for Live Announcement Templates 600a-600x used by the MNS Notification Engine 314 to generate Incident Templates 400a-400n and subsequent MNS Incidents 370a-370c in response to a triggering Event. Similar to the Message Template 500 described in relation to FIG. 5, the Live Announcement Template 600 may be one of the Notification Templates 410, 412, 414, 416, 418, or 420 shown in FIG. 4. In this example, the Live Announcement Template 600 is a type of Notification Template configured to hold pre-configured details of a Live Announcement that may be sent to the recipients 242 during an MNS Incident. In this example, the Live Announcement Template 600 is an object structure for holding the Notification's pre-configured General Settings 602, Control Options 604, recipient list 606, and Live Announcement Source 608. In this example, the Live Announcement Template 600 allows for the configuration of the object structure by the MNS Notification Engine as directed by the System Operator 304 using the UI 305. The General Settings 602 may include information, such as, for example, the name, description, and extended description of the Live Announcement. The Control Options 604 may be used by the MNS Notification Engine and MoCo Dispatcher to control the priority of the Live Announcement. The recipient list 606 may include rules as to which recipients 242 receive the Live Announcement. As an example, a rule restricting system end-devices may include limiting Live Announcements to only audio-enable devices such as loudspeakers. As another example, a rule restricting recipient groups may include limiting Live Announcements to only audio-enabled devices within those groups. Finally, as another example, a rule restricting recipient locations may include limiting Live Announcements to only audio-enabled devices within those locations.

Turning back to FIG. 3, the MoCo handler 308, 310, or 312 is generally a run-time software entity that supports one or more MNS Modalities and is responsible for delivering Notifications received from the Modality Corridor Dispatcher 316 to an MNS End-Point Address corresponding a respective MNS End-Point 380, 382, 384 or 386 via its System Intermediate Devices 318, 320, or 322, respectively. In general, the System Intermediate Device 318, 320, or 322 is a type of System Managed Device that supports the delivery of Notifications to MNS End-Devices. Examples of a System Intermediate Device may include a telephony card, Voice over Internet protocol ("VoIP") gateway device, media controller device (e.g., for LCD displays), text-to-speech device, SMTP email server, and VoIP switch device.

The term "MNS End-Device" is a general term for a System End-Device (such as, for example, system end-device 324 which may be, for example, a LED display, display monitor, flashing lights, bell, siren, loudspeaker, etc.) and recipient user end-device (such as, for example, recipient user end-device 326 which may be a cellular telephone, landline telephone, computer, tablet or other electronic communication device) which provides two functions: 1) Receive outbound Notifications from the MNS System and present them to the Recipients users 328 via the addressed MNS End-Point 380, 382, 384 or 386 within the MNS End-Device; and 2) Receive inbound Notifications from MNS Sources (not shown) (i.e., the recipient users 328), originating from an MNS End-Point's address, and deliver them to the Incident-centric MNS System 200. In general, the system intermediate devices 318, 320, and 322 in combination with MoCo handlers 308, 310, and 312, respectively, define modality corridors which are capable of processing one or more Modalities.

In this example, the System User 304 may be a system user which is trained to use the Incident-centric MNS System 200 and who administrates and operates the Incident-centric MNS System 200 in preparation for, and during Emergency Events. Similarly, a System Operator is a trained system user for operating the Incident-centric MNS System 200 during an Emergency Event, including initiating and managing MNS Incidents. Certain tasks of a System Operator can be automated through automated workflows, such as, for example, an Easy Trigger feature.

In operation, the System Users 304 operate the Incident-centric MNS System 200 for targeting Recipients 328 with Notifications through MNS End-Devices, for informing people about disruptions caused by Emergency Events. Recipients 328 may be defined in theRecipients List. System Users 304 may maintain their own contacts list for frequently-used recipients 328. In this example, there are four types of recipients 328: (1) Recipient Users, (2) Recipient Groups, (3) Locations, and (4) System End-Devices. A Recipient User 328 is a person that is a type of: (1) Recipient because the Incident-centric MNS System 200 is able to target them for Notifications; or (2) MNS User because they may interact with the Incident-centric MNS System 200 when receiving Notifications and when updating their profiles via the MNS Web interface. Notifications reach recipient users via their Recipient User End-Device, a.k.a. personal communication devices.

The Incident-centric MNS System 200 may also include at least one Modality Corridor that directs information from the MNS core logic module 306 to the recipient 242. The way that this information (both Outbound Notifications and Inbound Notifications) is directed from the MNS core logic module 306 to the recipients 242 and vise-versa is called the MNS Modality which is generally a delivery mode label, such as, for example, "SMS," "FAX," "E-MAIL," "PHONE," "WEB-FEED," etc. One or more MNS Modalities may be assigned to any valid combination of MNS end-point address and Notification Content Type, provided that the assigned modality has at least one supporting Modality Corridor.

In this example, three Modality Corridors 360, 362, and 364 may direct information from the MNS core logic module 306 to either system end-device 324 or recipient user end-device 326, or both. In this example, the first modality corridor 360 may include a corridor from the MoCo dispatcher 316, through the first MoCo handler 308 and system intermediate device(s) 318 to the system end-device 324 via signal paths 334, 340, and 346, respectively. Similarly, the second modality corridor 362 may include a corridor from the MoCo dispatcher 316, through the second MoCo handler 310 and system intermediate device(s) 320 to the system end-device 324 and recipient user end-device 326 via signal paths 336, 342, and 348, respectively. Moreover, the third modality corridor 364 may include a corridor from the MoCo dispatcher 316, through the first MoCo handler 312 and system intermediate device(s) 322 to the recipient user end-device 326 via signal paths 338, 344, and 350, respectively.

Figure 7:
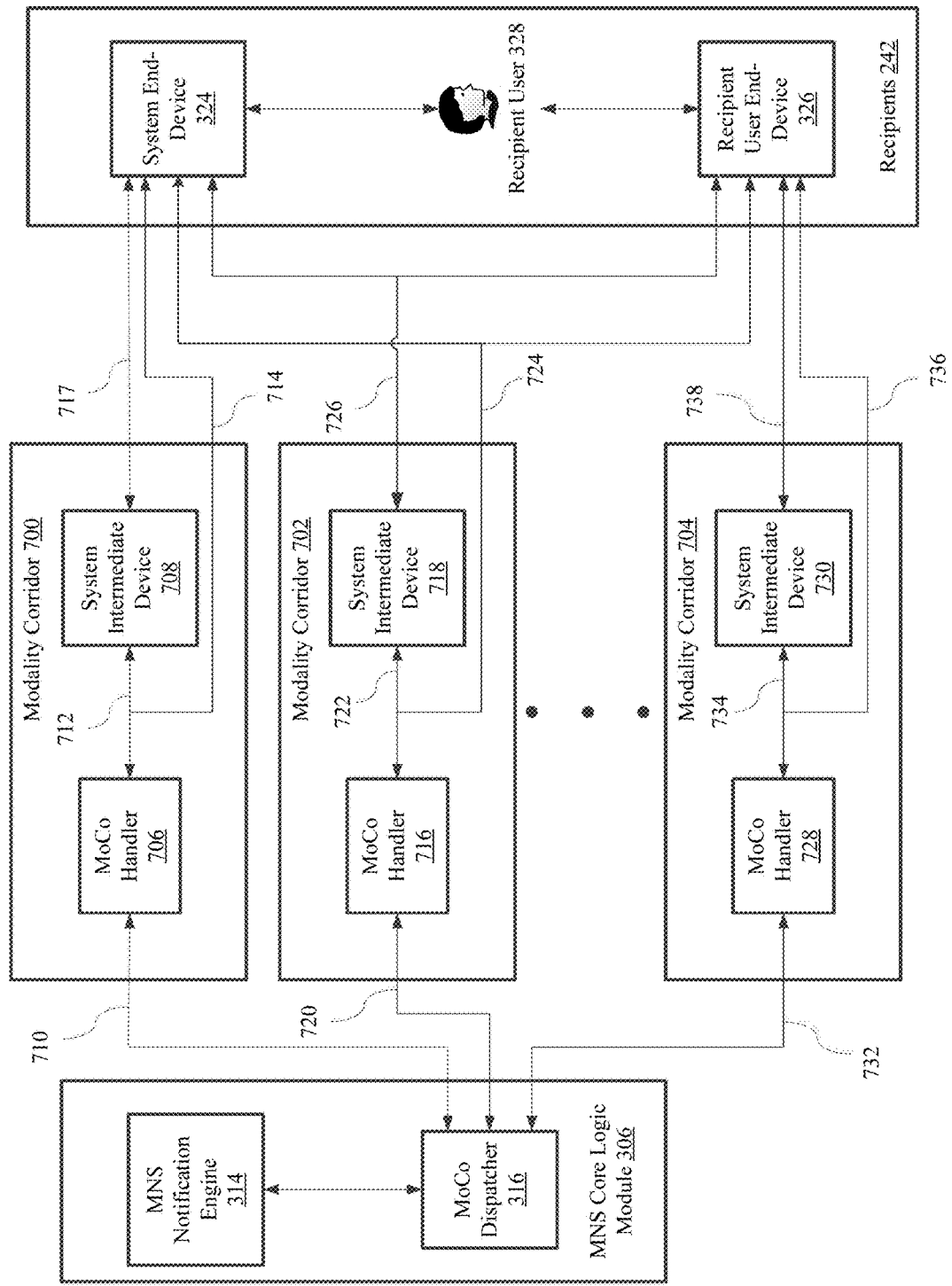
FIG. 7 is a block diagram of an example of an implementation of the Modality Corridors of Incident-centric MNS System shown in FIG. 3 in accordance with invention.

In FIG. 7, a block diagram of an example of an implementation of the Modality Corridors 700, 702, and 704 of Incident-centric MNS System 200, of FIG. 3, is shown. In this example, the first modality corridor 700 may include a MoCo handler 706 and at least one system intermediate device 708. The first MoCo handler 706 may be in signal communication with the MoCo dispatcher 316, system intermediate device 708, and system end-device 324 via signal paths 710, 712, and 714, respectively. The system intermediate device 708 may also be in signal communication with the system end-device 324 via signal path 717. Similarly, the second MoCo handler 716 may be in signal communication with the MoCo dispatcher 316, system intermediate device 718, system end-device 324, and recipient user end-device 326 via signal paths 720, 722, and 724, respectively. The system intermediate device 718 may also be in signal communication with the system end-device 324 and the recipient user end-device 326 via signal path 726. Moreover, the third MoCo handler 728 may be in signal communication with the MoCo dispatcher 316, system intermediate device 730, and recipient user end-device 326 via signal paths 732, 734, and 736, respectively. The system intermediate device 730 may also be in signal communication with the recipient user end-device 326 via signal path 738. In this example, a signal intermediate device is shown in the modality corridor; however, it should be noted that each modality corridor 700, 702, and 704, may include more than one system intermediate device.

Figure 8:
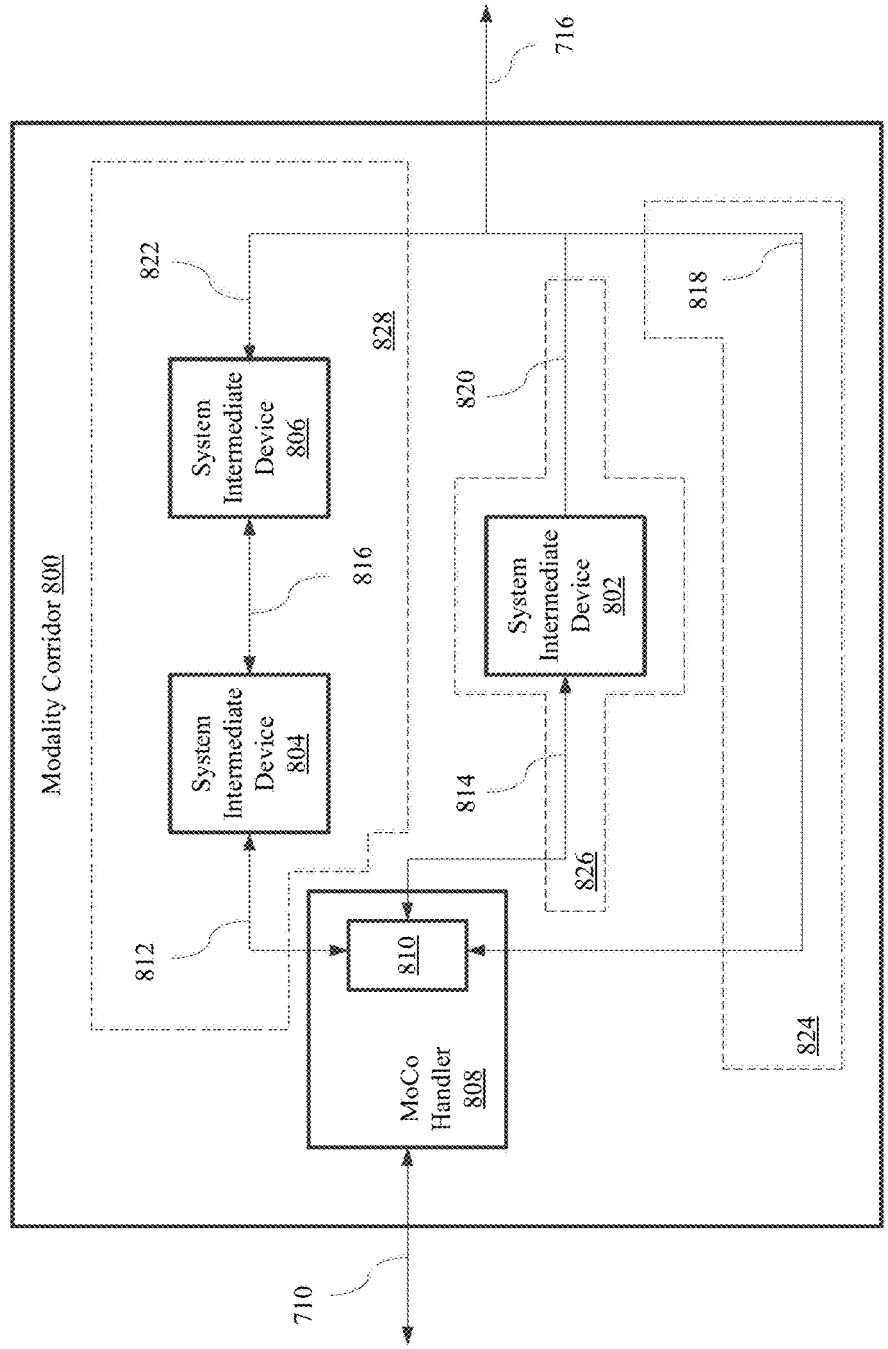
FIG. 8 is a block diagram of an example of an implementation of a Modality Corridor shown in FIG. 4 having multiple system intermediate devices in accordance with invention.

Turning to FIG. 8, a block diagram of an example of an implementation of a Modality Corridor 800 is shown having multiple system intermediate devices 802, 804, and 806. In this example, the modality corridor 800 may include a MoCo handler 808 and the system intermediate devices 802, 804, and 806. The MoCo Corridor 800 may be an implementation of either the first modality corridor 700, second modality corridor 702, or third modality corridor 704 shown in FIG. 7. In an example of implementation of the first modality corridor 700, the MoCo Corridor 800 may be in signal communication MoCo dispatcher 316 and System end-device 324 via signal paths 710, 714 and 717. In this example, the MoCo handler 808 may include a Delivery Path Router 810. The Delivery Path Router 810 may be in signal communication with the first system intermediate device 802 and second system intermediate device 804 via signal paths 814 and 812, respectively. The second intermediate device 804 may be in signal communication with the third intermediate device 806 via signal path 816. The Delivery Path Router 810, first system intermediate device 802, and third system intermediate device 806 may be in signal communication with the system end-device 324 via signal paths 818, 820, and 822, respectively that combine to become signal path 717. In this example, a first modality delivery path 824 may be defined between the delivery path router 810, through signal path 818, to signal path 716. In this first modality delivery path 824 there are no system intermediate devices and the information passes directly from the MoCo handler 808 to the System end-device 324 through signal paths 818 and 717 (which are appreciated to be the same signal path in this example). The second modality delivery path 826 may be defined between the delivery path router 810, through the signal path 814, first intermediate device 802, and signal path 820 to signal path 717. In this second modality delivery path there is only one system intermediate device between the Delivery Path Router 810 to the system end-device 324. Furthermore, the third modality delivery path 828 may be defined between the delivery path router 810, through signal path 812, second system intermediate device 804, third system intermediate device 806, and signal path 822 to signal path 717. In this third modality delivery path there may be a plurality of system intermediate devices between the Delivery Path Router 810 to the system end-device 324. In this example, two system intermediate devices 804 and 806 are shown but it is appreciated that more than two system intermediate devices may be utilized without departing from the spirit of the invention.

Figure 9A:
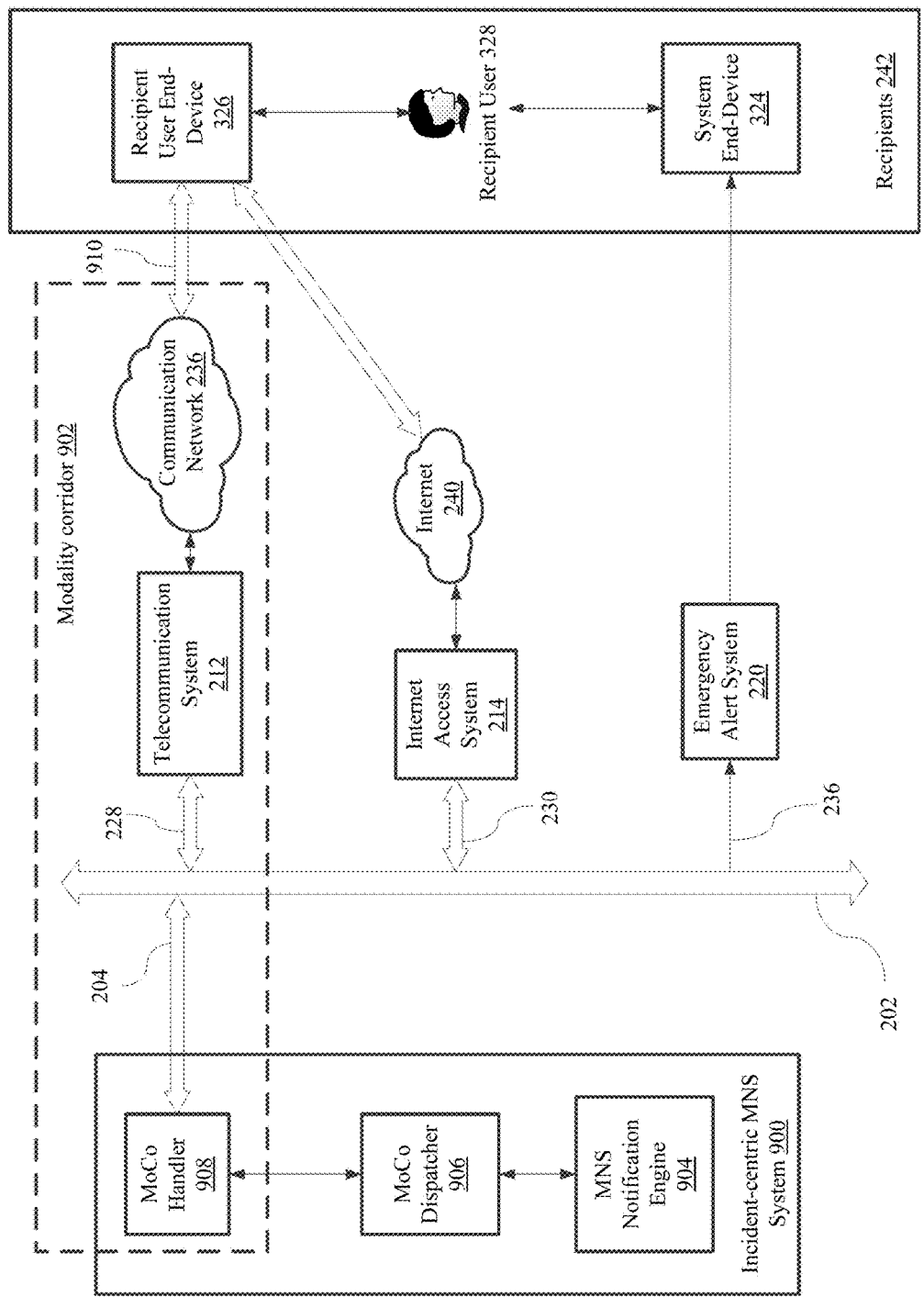
FIG. 9A is a block diagram of an example of an implementation of the process performed by the Incident-centric MNS system utilizing a first modality corridor across the facility network shown in FIG. 2 in accordance with invention.

In FIG. 9A, a block diagram of an example of an implementation of the process performed by the Incident-centric MNS system 900 utilizing a first modality corridor 902 across the facility network 202, of FIG. 2, is shown. In this example, the incident centric MNS systems 900 may include the MNS Notification Engine 904, MoCo dispatcher 906, and MoCo handler 908. The MNS Notification Engine 904 and MoCo dispatcher 906 may be part of a MNS core logic module (shown in FIGS. 3 and 7). In this example the first Modality Corridor 902 extends between the MoCo handler 908 and the Recipient user end-device 326 via the facility network 202, telecommunication system 212, and communication network 236. MNS information is generated by the Incident-centric MNS system 900 and passed from the MoCo dispatcher 906 to the first modality corridor 902 via MoCo handler 908. In this example, there may be multiple modality corridors, of which only one (first modality corridor 902) is shown for simplicity and illustrative purposes. The MoCo handler 908 may include a Delivery Path Router (not shown but described above in relation to Delivery Path Router 810 in FIG. 8) that determines a modality delivery path through the first Modality Corridor 902. In this example, the modality delivery path may be from the MoCo handler 908 to recipient user end-device 326 through signal path 204, facility network 202, signal path 228, telecommunication system 212, communication network 236 and signal path 910. In this example, the modality corridor 902 may include one or more system intermediate devices (not shown) as described above in relation to FIG. 8.

In a further example of operation, the MNS Notification Engine 904 may produce a Notification (e.g., 374f in FIG. 3) associated with an MNS Incident (e.g., 370c in FIG. 3) that there is a fire within the facility. The MoCo dispatcher 906 may then choose (based on a predetermined and/or preselected notification rule) to send a pre-recorded voice message associated with the Notification to the recipient user 328 via a registered cellular telephone number of the cellular telephone (i.e., the recipient user end-device 326) of the recipient user 328. In the example scenario, the MoCo dispatcher 906 would chose to utilize the first modality corridor 902 that passes through the telecommunication system 212, which may include a way to communicate with the cellular telecommunication network (i.e., communication network 236) corresponding to the recipient user end-device 326 of the recipient user 328. In this example, the pre-recorded voice message would be passed to the recipient user end-device 326 allowing the recipient user 328 to hear the pre-recorded voice message.

Figure 9B:
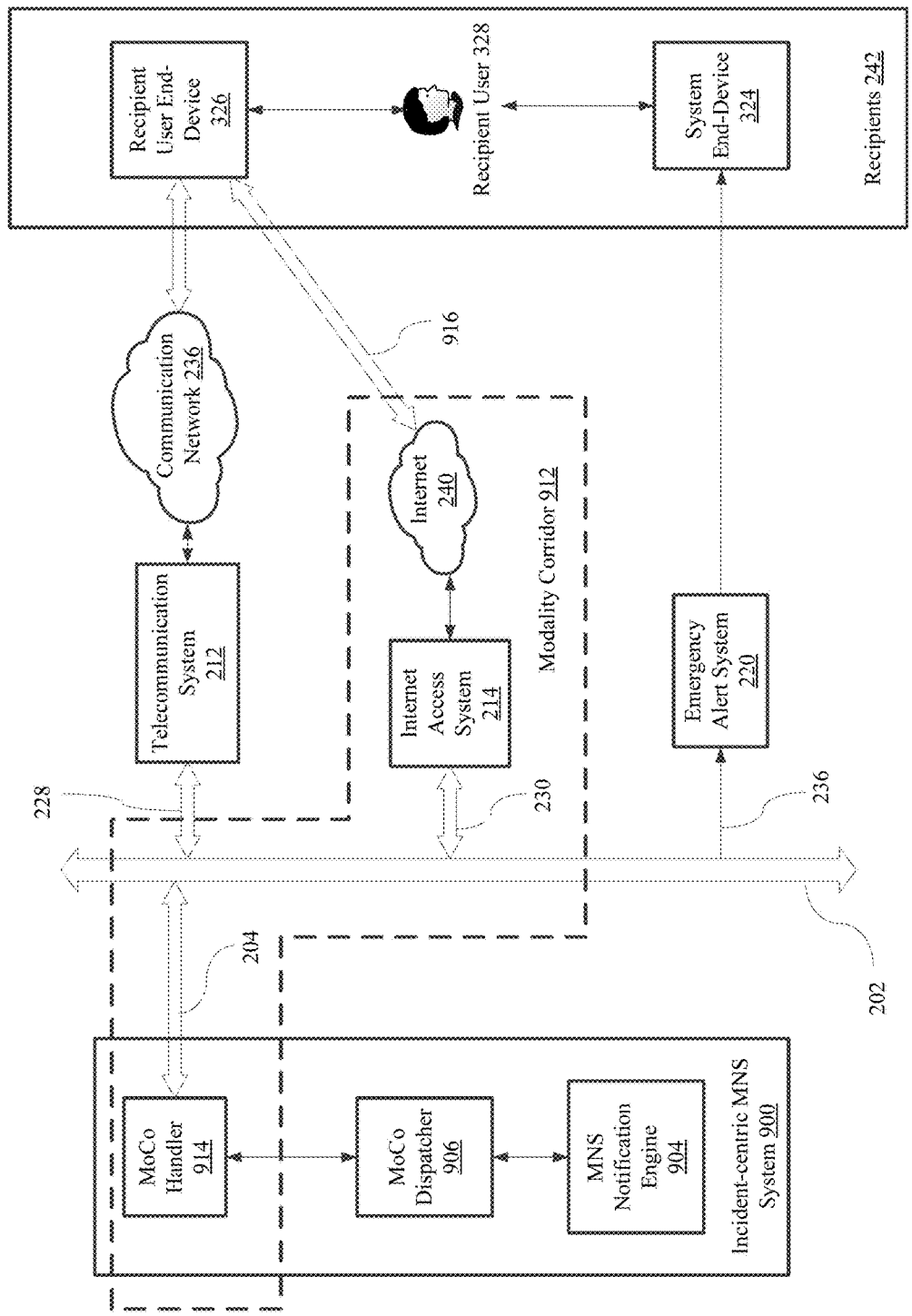
FIG. 9B is a block diagram of an example of an implementation of the process performed by the Incident-centric MNS system utilizing a second modality corridor across the facility network shown in FIG. 2 in accordance with invention.

In FIG. 9B, a block diagram of an example of an implementation of the process performed by the Incident-centric MNS system 900 utilizing a second modality corridor 912 across the facility network 202, of FIG. 2, is shown. The process described in FIG. 9B is similar to the one described in FIG. 9A, except that in this example the second modality corridor 912 extends between the MoCo handler 914 and the Recipient user end-device 326 via the facility network 202, Internet Access System 214, and Internet 240. In this case, MNS information is generated by the Incident-centric MNS system 900 and passed from the MoCo dispatcher 906 to the second modality corridor 912 via MoCo handler 914. Again, in this example, there may be multiple modality corridors, of which only one (second modality corridor 914) is shown for simplicity and illustrative purposes. In this example, the MoCo handler 914 may include a Delivery Path Router (not shown but described above in relation to Delivery Path Router 810 in FIG. 8) that determines a modality delivery path through the second Modality Corridor 912. In this example, the modality delivery path may be from the MoCo handler 914 to recipient user end-device 326 through signal path 204, facility network 202, signal path 230, Internet Access System 214, Internet 240 and signal path 916. In this example, similar to the example described above in relation to FIG. 9A, the second modality corridor 912 may include one or more system intermediate devices (not shown) as described above in relation to FIG. 8.

As a further example of operation, the MNS Notification Engine 904 may again produce a Notification 374f associated with an MNS Incident 370c that there is a fire within the facility. The MoCo dispatcher 906 may then choose (based on a predetermined and/or preselected notification rule) to send a pre-determined email message associated with the Notification to the recipient user 328 via a registered Internet device (i.e., the recipient user end-device 326 such as a computer, smart cellphone, tablet, etc.) of the recipient user 328. In the example scenario, the MoCo dispatcher 906 would chose to utilize the second modality corridor 912 that passes through the Internet Access system 214, which may include any way to communicate with the Internet 240. In this example, the pre-determined email message would be passed to the recipient user end-device 326 allowing the recipient user 328 to see the email message.

Figure 9C:
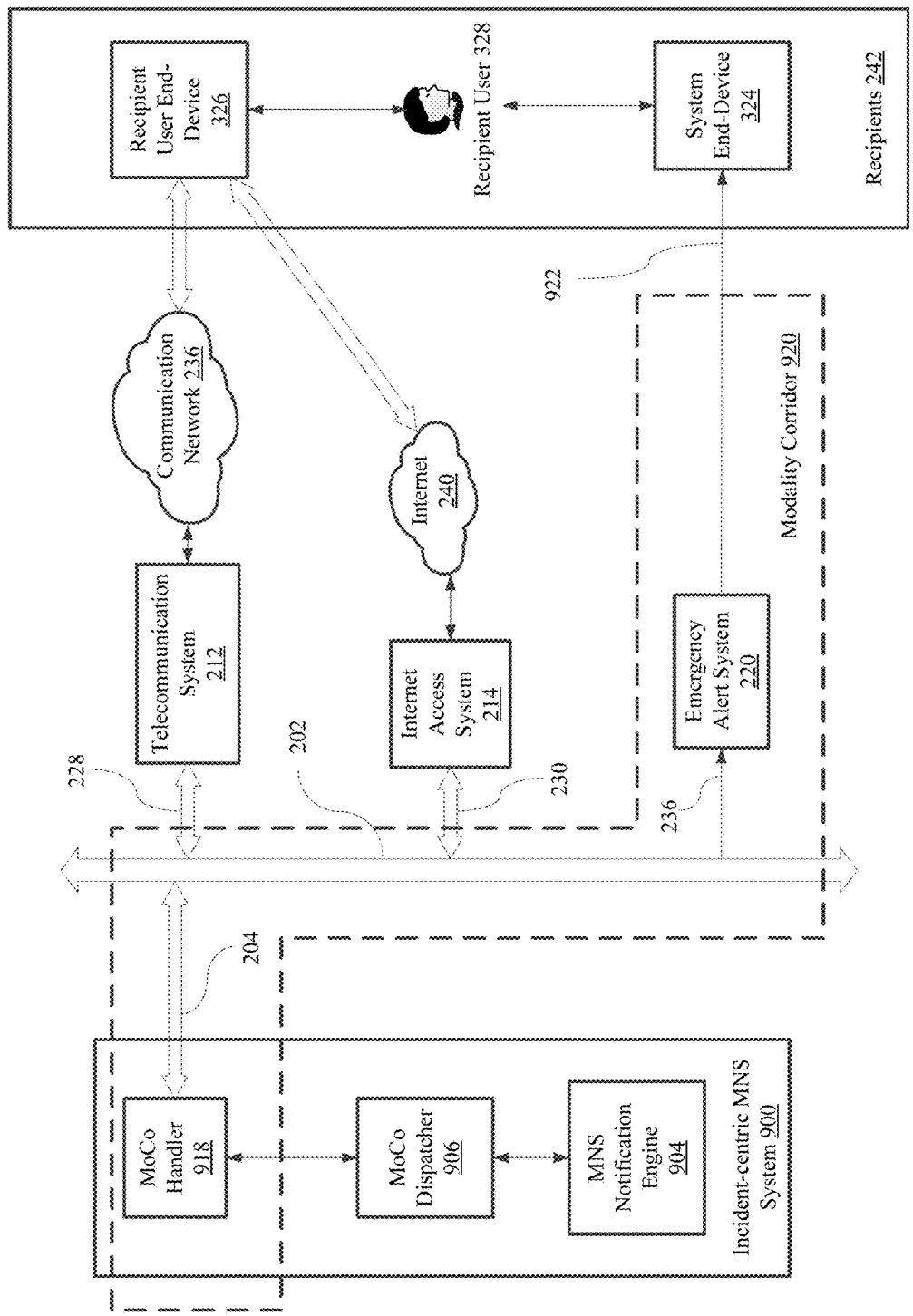
FIG. 9C is a block diagram of an example of an implementation of the process performed by the Incident-centric MNS system utilizing a third modality corridor across the facility network shown in FIG. 2 in accordance with invention.

Turning to FIG. 9C, a block diagram of an example of an implementation of the process performed by the Incident-centric MNS system 900 utilizing a third modality corridor 920 across the facility network 202, of FIG. 2, is shown. The process described in FIG. 9C is similar to the ones described in FIGS. 9A and 9B, except that in this example the third modality corridor 920 extends between the MoCo handler 918 and the System end-device 324 via the facility network 202 and the emergency alert system 220. In this case, MNS information is generated by the Incident-centric MNS system 900 and passed from the MoCo dispatcher 906 to the third modality corridor 920 via MoCo handler 918. In this example, the MoCo handler 918 may include a Delivery Path Router (not shown but described above in relation to Delivery Path Router 810 in FIG. 8) that determines a modality delivery path through the third Modality Corridor 920. In this example, the modality delivery path may be from the MoCo handler 918 to the System end-device 324 through signal path 204, facility network 202, signal path 236, Emergency Alert System 220, and signal path 922. In this example, similar to the examples described above in relation to FIGS. 9A and 9B, the third modality corridor 920 may include one or more system intermediate devices (not shown) as described above in relation to FIG. 8.

As a further example of operation, the MNS Notification Engine 904 may again produce a Notification 374f associated with an MNS Incident 370c that there is a fire within the facility. The MoCo dispatcher 906 may then choose (based on a predetermined and/or preselected notification rule) to send a pre-determined message associated with the Notification to the recipient user 328 via the Emergency Alert System 220 such may be a generic alarm notification system that drives the system end-device 324, which may include bells, horns, lights, loudspeakers, and/or sirens. In the example scenario, the MoCo dispatcher 906 would chose to utilize the third modality corridor 920 that passes through the Emergency Alert System 220, which would allow a System Operator (not shown) to deliver a Live Announcement type of Notification to the recipients 242, which an individual recipient user 328 may receive via the system end-device 324.

Figure 10:
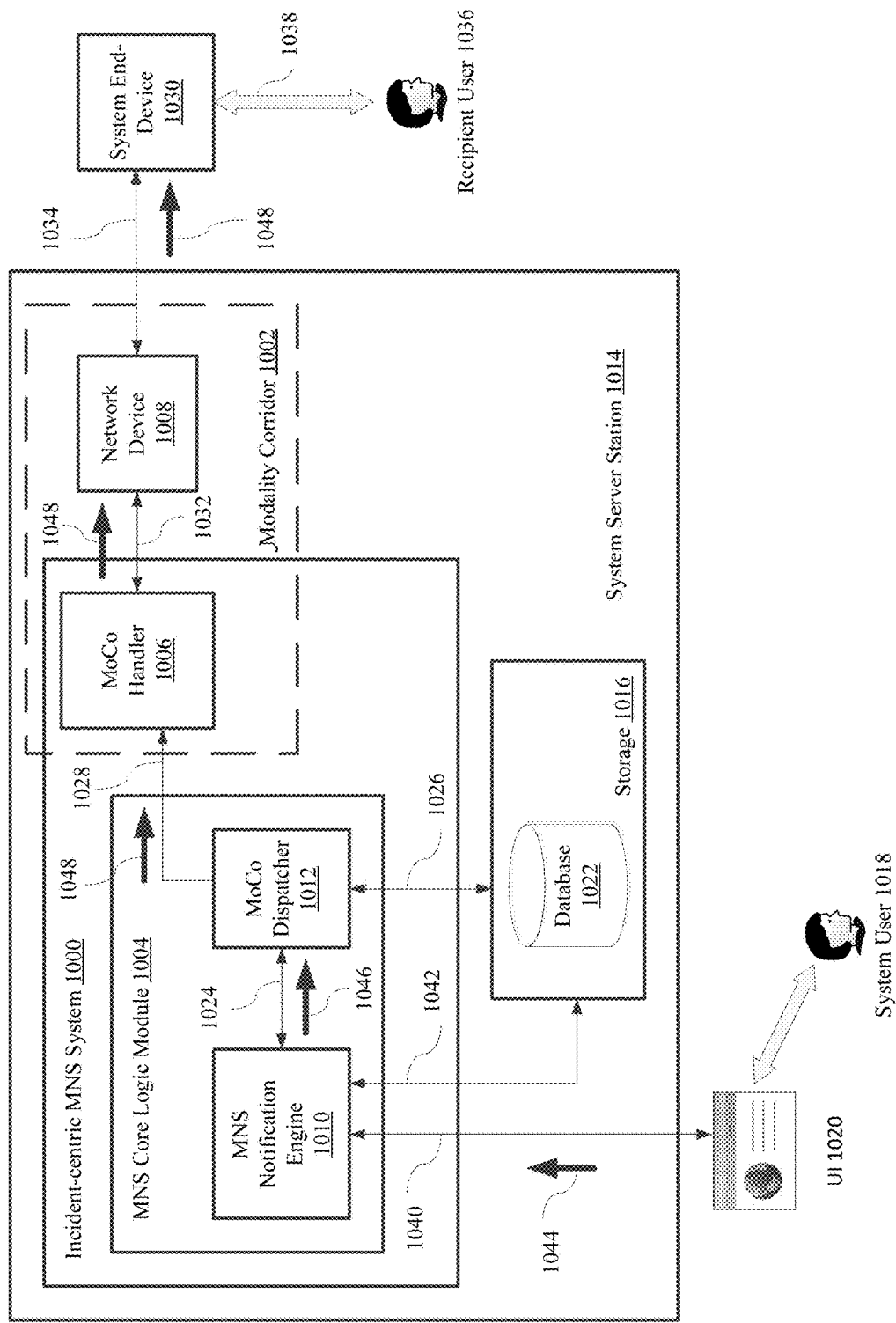
FIG. 10 is a block diagram of example of operation of the Incident-centric MNS System along a modality corridor in accordance with the invention.

Turning to FIG. 10, a block diagram of example of operation of the Incident-centric MNS System 1000 along a modality corridor 1002 is shown. This example is similar to the example shown in FIG. 3. In this example the Incident-centric MNS System 1000 may include a MNS logic Module 1004 and a MoCo Handler 1006. The MoCo Handler 1006 and a System Intermediate Device are part of the Modality Corridor 1002. In this example, the System Intermediate Device may be a network device 1008. The MNS Core Logic Module 1004 may include a MNS Notification Engine 1010 and MoCo Dispatcher 1012. The Incident-centric MNS System 1000 may be a device, component, software module, or combination of hardware and software device located within a System Server Station 1014. The System Server Station 1014 may be computer system having a processor (not shown), storage device 1016, random access memory (not shown), communication buses (not shown), and input output communication interfaces (not shown). At least one of the input/output communication interfaces allows a System User 1018 to utilize a UI 1020 to communicate with the Incident-centric MNS System 1000. In this example the storage device 1016 may include at least one database 1022.

In this example, the MoCo Dispatcher 1012 may be in signal communication with the MNS Notification Engine 1010, Storage device 1016, and MoCo Handler 1006 via signal paths 1024, 1026, and 1028, respectively. The network device 1008 may be in signal communication with the MoCo Handler 1006 and a System End-Device 1030 via signal paths 1032 and 1034, respectively. A Recipient User 1036 may interface with the System End-Device 1030 either through signal path 1038 or physically (i.e., view visual information or hear sounds and/or announcements). The UI 1020 may be in signal communication with the MNS Notification Engine 1010 via signal path 1040 and the MNS Notification Engine 1010 may also be in signal communication with storage device 1016 via signal path 1042.

In this example, the System End-Device 1030 is a visual display (such as an LED display) or audio device (such as a loudspeaker or siren). The System End-Device is a device (as stated earlier) that has an MNS End-Point Address for an MNS End-Point (such as 380 or 382 in FIG. 3). In this example, this MNS End-point Address may be a TCP/IP address, such as, for example, 192.168.0.XXX, where XXX represent a number from 0 to 999. This address may be stored in the database 1022. Since in this example the MNS End-point Address has been chosen to be a TCP/IP address, the signal path 1034 may be along an Ethernet network and/or the Internet. As such, the network device 1008 may be a known interface device that allows the System Server Station 1014 to communicate with the Ethernet network/Internet along signal path 1034.

In an example of operation, once an Emergency Event happens, the MNS Notification Engine 1010 may instantiate an MNS Incident (such as 370a in FIG. 3) which may be utilized by the System User 1018, via the UI 1020, to manage and keep track of the Emergency Event. Responses from the System User 1018 to the MNS Notification Engine 1010, via the UI 1020, are shown as User signals 1044 along signal path 1040. In response to the MNS Incident, the MNS Notification Engine 1010 sends Notifications (e.g., 372a-372f in FIG. 3) associated with the MNS Incident (e.g., 370a) to the Recipient User 1036 via the System End-Device 1030 to keep the Recipient User 1036 informed during the Emergency Event. In this example, the Notifications are Live Announcements since in this example the System End-Device 1030 is either a visual display or audio device. These Notifications are sent to the System End-Device 1030 by first sending a Notification signal 1046 corresponding to the Notifications associated with the respective MNS Incident from the MNS Notification Engine 1010 to the MoCo Dispatcher 1012 via signal path 1024.

Since in this example, the Notification sent by the MNS Notification Engine 1010 is a Live Announcement, the Notification is a real time audio stream from the System User 1018. The Notification may include pre-configured details of the Live Announcements which may be stored in Live Announcement Templates (e.g., pre-configured ones of Live Announcement Templates 600a-600z). The Live Announcement Template may be stored in the storage device 1016. As such, the Notification signal 1046 includes information related to the real time audio stream from the System User 1018 and the pre-configured details of the Live Announcement which are stored in Live Announcement Templates. However, in this example, Notification signal 1046 does not include address information for the System End-Device 1030. Once the Notification signal 1046 is received by the MoCo Dispatcher 1012, the MoCo Dispatcher 1012 determines which modality corridor to utilize in reaching the System End-Device 1030. In this figure, only one modality corridor 1002 is shown for convenience and it is appreciated that plurality of modality corridors may be shown as in FIGS. 3, 7, 9A, 9B, and 9C.

In this example, the MoCo Dispatcher 1012 establishes a signal path from the MNS Notification Engine 1010 to the System End-Device 1030 through the Modality Corridor 1002. The MoCo Dispatcher 1012 receives the Notification signal 1046 and recognizes the need for the address information corresponding to the MNS End-Point (e.g., 380) of the System End-Device 1030. The MoCo Dispatcher 1012 then acquires the address information for the MNS End-Point (e.g., 380) of the the System End-Device 1030 from the database 1022 and transforms the Notification signal 1046 into addressed Notification signal 1048 that is sent to the MoCo Handler 1006. The MoCo Handler 1006 and network device 1008 then sends the addressed Notification signal 1048 to the System End-Device 1030 via signal paths 1032 and 1034. Once the MNS End-Point (e.g., 380) of the System End-Device 1030 receives the addressed Notification signal 1048, the System End-Device 1030 displays or transmits the Live Announcement to the Recipient User 1036.

Figure 11:
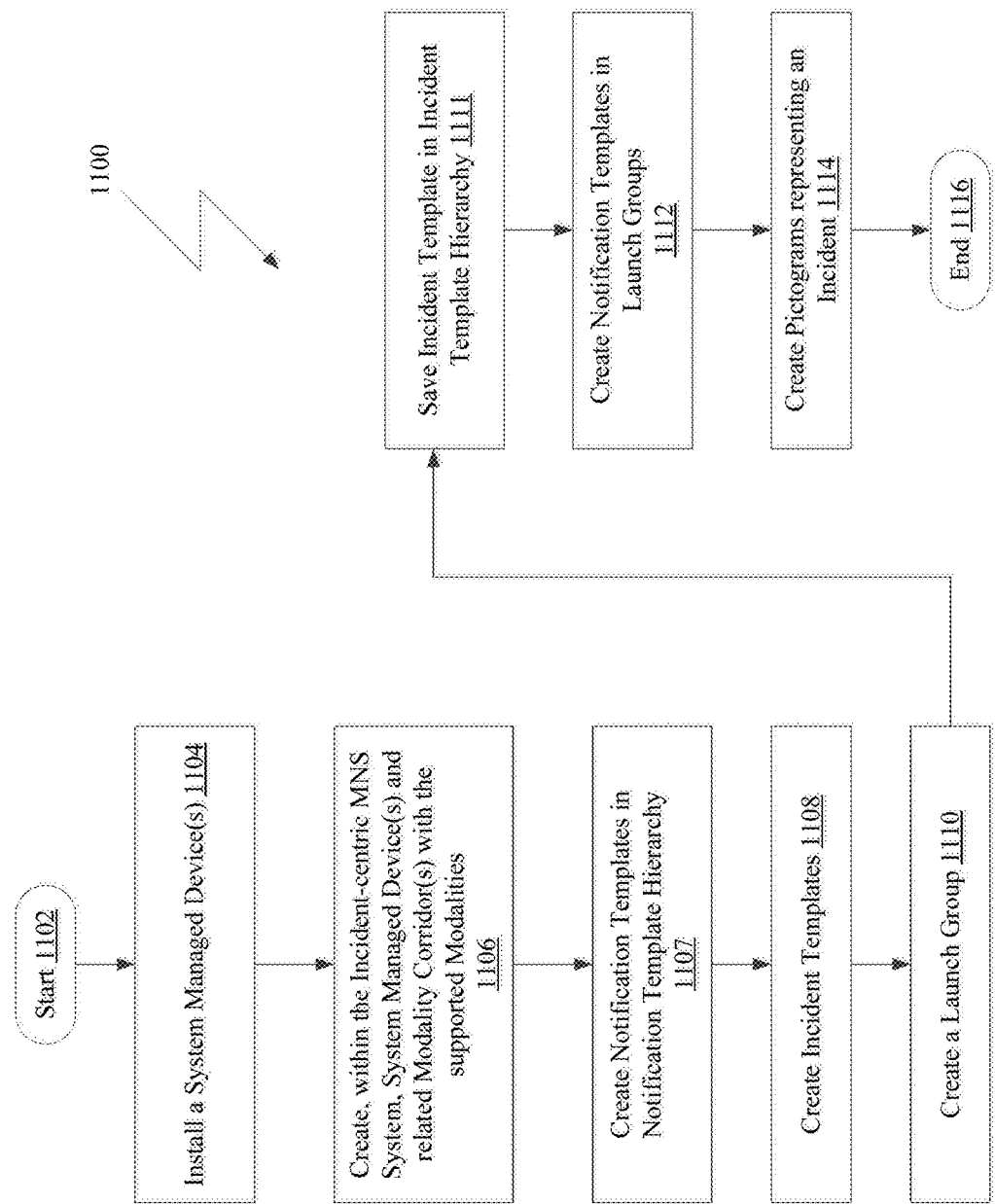
FIG. 11 is a flowchart of an example of an implementation of a process performed in setting up an example Incident object in the Incident-centric MNS system, shown in FIGS. 2 and 3, in accordance with the invention.

In FIG. 11, a flowchart 1100 is shown of an example of an implementation of a process performed in setting up an example MNS Incident in the Incident-centric MNS system 200 of FIGS. 2 and 3. The process may start 1102, where a MNS User (such as a Customer Service Representative ("CSR") Installer or System Administrator) installs one or more System Managed Devices 1104 for signal communication with the Incident-centric MNS system 200, where a System Managed Device is a System End-Device or a System Intermediate Device. Then in step 1106, the MNS User creates, within the Incident-centric MNS System, System Managed Device(s) and related Modality Corridor(s) with the supported Modalities. The System Managed Devices consists of System End-Devices and System Intermediate Devices, where the Modality Corridor(s) support the delivery of Notifications to System End-Devices and Recipient End-Devices. In step 1107, the MNS User using the UI 305 and MNS Notification Engine 314 creates Notification Templates in the Notification Template Hierarchy (e.g., 500a-500z and 600a-600x) and configures these templates with information such as General Settings 502, 602, Control Options 504, 604, Scheduler 506, Recipient List 508, 606, and Content 510.

Once the Notification Templates have been created within the Incident-centric MNS system, the MNS User may use the UI 305 and the MNS Notification Engine 314 to create an Incident Template in step 1108. This example Incident Template may be the same as the example described previously in Incident Template 400 in FIG. 4. Again, the Incident Template is an object structure for holding the Incident Template's pre-configuration Notification Templates for generating the same for a subsequent MNS Incident when instantiated by the MNS Notification Engine. These pre-configured Notification Templates are organized within the Incident Template Content 402 of the respective Incident Template that includes at least one Launch Group which may be known as a START Launch Group and may also include a Trigger Rule 422 and/or Dial Menu. As stated earlier, the Trigger Rule describes the conditions for which a Trigger Incident shall occur, where the Trigger Incident is an automatic initiation of MNS Incidents or Incident objects by the MNS Notification Engine 314 based on an inbound notification to the Incident-centric MNS System. These Trigger Incidents may be configured to require human interaction to confirm the initiation of an automatically Triggered Incident. The dial menu may be a dial-in feature that may be utilized by the System Operator to easily and quickly cause the MNS Notification Engine 314 to initiate MNS Incidents and launch associated Notifications via a telephone.

Once the Incident Template is created, the MNS User may use the UI 305 and MNS Notification Engine to create one or more launch groups in step 1110 as shown in FIG. 4 (which shows, as an example, three launch groups LG1 404 through LG3 408). Again utilizing the example shown in FIG. 4, LG1 404 may be the designated START Launch Group that includes Notification Templates 410 through 412 that will be launched when an MNS Incident is initiated by the MNS Notification Engine 314. LG2 406 may be the update Launch Group that includes Notification Templates 414 through 416 that will be launched by the MNS Notification Engine 314 during the course of the corresponding MNS Incident (e.g., 370*a*) in response to the Emergency Event. The designation of update Launch Groups for an MNS Incident are at the discretion of the System Operator 304 using the MNS Notification System 314 in order, to provide further updates to the Recipients. LG3 408 may be the designated CLEAR-ALL Launch Group that will be launched when the System Operator 304 has started to close the respective MNS Incident, resulting in the launch of all the Notifications in this Launch Group for that MNS Incident, followed by all active Notifications within this incident reaching the state of Canceled or Expired, after which the MNS Incident will reach the state Closed. Once the Launch Groups are created and associated with the respective Incident Template in step 1110, the MNS User using the UI 305 in cooperation with the MNS Notification Engine 314 may cause the Incident Template to be saved, in step 1111, into the Incident Template Hierarchy 500*a*-500*z* and 600*a*-600*x* for later use by the Incident-centric MNS System 200, 900 or 1000 and the process continues to step 1112.

Once a launch group is created for a respective Incident Template, the MNS User, in step 1112, may also use the US 305 to cause the MNS Notification System 314 to create one or more Notification Templates (e.g., 410-412, 414-416, and 418-420) within a given launch group (e.g., 404, 406, and 408) as shown in FIG. 4, where each Notification Template is an object structure for holding, for a given MNS Incident Template, the Notification's (e.g., 370*a*) pre-configured Control Options, Scheduler settings, recipients, and Content: TEXT, AUDIO, and MULTIMEDIA. The MNS User, in step 1114, may then also use the UI 305 to cause the MNS Notification Engine 314 to create one of more pictograms representing an MNS Incident such as a fire, storm, chemical spill, etc. as described in relation to FIG. 4. As described previously, these pictograms may be quick launch or "Easy Trigger" graphical pictograms on the UI 305 of terminal 302 that represent different types of Emergency Events for which a System Operator may quickly need to cause the MNS Notification Engine 314 to initiate MNS Incidents and launch associated Notifications. More specifically, these pictographs may be associated ("linked") to an Incident Template (e.g., 400*a*) in the Incident Template Hierarchy 400*a*-400*n*, so that clicking on any of these pictograms when displayed by the UI 305 is effectively the same as navigating to the associated Incident Template (e.g., 400*a*) in the Incident Template Hierarchy 400*a*-400*n* and clicking "Initiate". The process then ends 1116.

As an example of an implementation of this process, an example Emergency Event may be a hurricane and the Incident-centric MNS system 200, 900 or 1000 may be programmed with an emergency management plan that calls for sending five types of Notifications (messages) in case of a hurricane that include: 1) Warning that a hurricane is approaching; 2) Warning that damage to the building has occurred/repaired; 3) Warning that power to the building has been lost; 4) Notification that power to the building has been restored; and 5) Notification that the hurricane warning has been lifted. In this example, the UI 305 and MNS Notification Engine 314 may be used to perform the process 1100 to generate five Notification Templates (e.g., 500*a*-500*e*) in step 1107, and store each in the Notification Template Hierarchy 500*a*-500*z* and 600*a*-600*x*. Then, in step 1112 these five Notification Templates would be copied by the MNS Notification Engine 314 into the respective Launch Groups for the respective Incident Template (e.g., 400*a*); each Notification Template may also be edited by an MNS User as needed using the UI 305 in cooperation with the MNS Notification Engine 314 so that when the Notification Template is a Message Template, the Message Template's recipient will be set to the corresponding Recipient User, Location, Group, or system end-device. The text of these five Notification Templates may be edited such that the text of each Notification Templates may reflect its specific purpose.

In this example, an emergency management team may decide to create distinct Incident Templates to provide different sets of information related to the general Event of a hurricane. As an example, three distinct Incident Templates may be created using the MNS Notification Engine that include, for example, 1) a hurricane Incident Template, 2) a building damage Incident Template, and 3) a power loss Incident Template.

In this example for the hurricane Incident Template, two Launch Groups may be created for this Incident Template, in step 1110, that include a first Launch Group 404 that is an "approaching hurricane warning" launch group and a second Launch Group 406 that is a "lifted hurricane warning" launch group. In this example, each Launch Group may contain only one Notification Template. It is appreciated that the choice of two Launch Groups and one Notification Template is for ease of illustration and does not limit the number of potential Launch Groups or Notification Templates in each Launch Group for a respective Incident Template.

Additionally, in this example for the building damage Incident Template, only one Launch Group may be created, in step 1110, that is a "building damage update" Launch Group that contains one Notification Template. In this example, the MNS Incident's (e.g., 370*a*) Notification (e.g., 372*a*) corresponding to this Notification Template (e.g., 410) may carry a user variable that may be set during launch of the MNS Incident to indicate the specific damage to the building. Again, it is appreciated that the choice of one Launch Group and one Notification Template is for ease of illustration and does not limit the number of potential Launch Groups or Notification Templates in a building damage Incident Template or each Launch Group, respectively.

Moreover, in this example for the power loss Incident Template, two Launch Groups may be created, in step 1110, that include a first Launch Group that is a "power lost" Launch Group that contains one Notification Template and a second Launch Group that is a "power restored" Launch Group which also contains one Notification Template. In this example the first "power lost" Launch Group may be designated as the "START" Launch Group as described above. Again, it is appreciated that the choice of two Launch Groups and one Notification Template is for ease of illustration and does not limit the number of potential Launch Groups or Notification Templates in each Launch Group.

Once these Incident Templates are created, pictograms (i.e., "Easy Buttons") may be created, in step 1114, that represent the different Incident Templates. Specifically, a first Easy Button may be created for the Incident Template "Hurricane Warning," a second Easy Button may be created for the Incident Template "Building Damage," and a third Easy Button may be created for the Incident Template "Power Outage."

Figure 12:
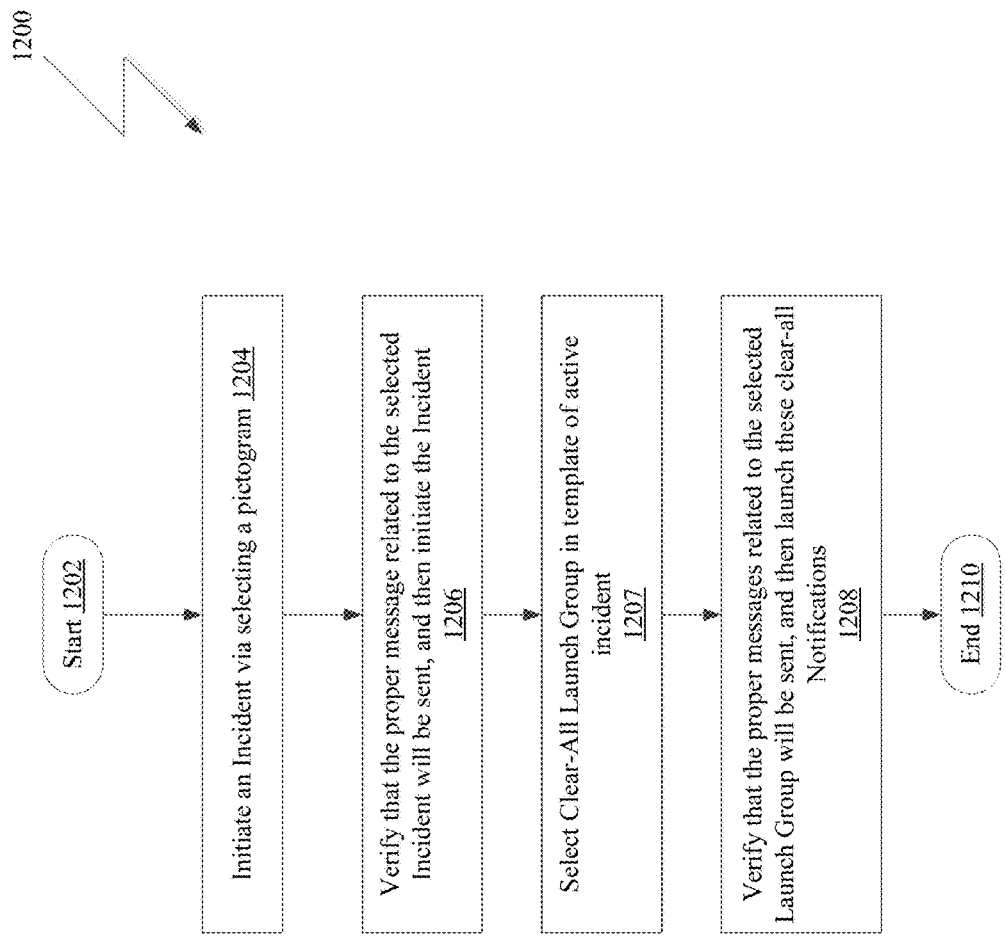
FIG. 12 is a flowchart of an example of an implementation of a process performed by the Incident-centric MNS system in operation on the set-up example Incident, described in FIG. 10, in accordance with the invention.

Turning to FIG. 12, a flowchart 1200 of an example of an implementation of a process performed by the Incident-centric MNS system 200, 900 or 1000 is shown. In this example, the process performed by the Incident-centric MNS system is in relation to the example hurricane Emergency Event and corresponding MNS Incidents described above in relation to FIG. 11.

The process may start 1202, where a System User causes the MNS Notification Engine to initiate a "hurricane" MNS Incident in response to a corresponding Emergency Event by selecting, in step 1204, the preprogrammed pictogram (i.e., the first Easy Button described above in relation to FIG. 11) that corresponds to the Incident Template "Hurricane Warning" previously created in the Incident-centric MNS system in the performance of process 1100. The System User then verifies, in step 1206, that the proper message will be sent, which corresponds to the Incident Template "Hurricane Warning." The System User verifies this by selecting to initiate the MNS Incident in response to a query from the Incident-centric MNS System in response to the System User selecting the pictogram corresponding to the Incident Template "Hurricane Warning." Once the Emergency Event (i.e., the hurricane event) has ended, the System User selects the Clear-All Launch Group in the active incident 1207, verifies that the proper messages related to the selected Launch Group will be sent, and then launches these clear-all Notifications 1208, indicating that the Incident has ended.

In this example, the System User uses the UI 305 to navigate to the Clear-All Launch Group for the active MNS Incident. The System User then selects this Launch Group by clicking "Launch" on UI 305. The UI 305 then presents to the System User a list of Notifications that will be sent, and these Notifications can be optionally further customized by the System User. Once the System User agrees with the messages that are to be sent, the System User may click the confirmation button and that starts the launch process. This launch process may be the same for any launch groups that is selected.

In this example, after the Clear-All launch group has been launched, it will not only sent the Notifications it contains (as per the above description), but it will also cause the cancelation of any other active Notification. In other words, launching the Clear-All Launch Group is a one-stop place for the operator to wrap up the MNS Incident forcefully, so that the MNS Incident moves into state Completed and recipients have been informed that the situation is OK. After that the System User can close the MSN Incident. The process then ends 1210.

Figure 13:
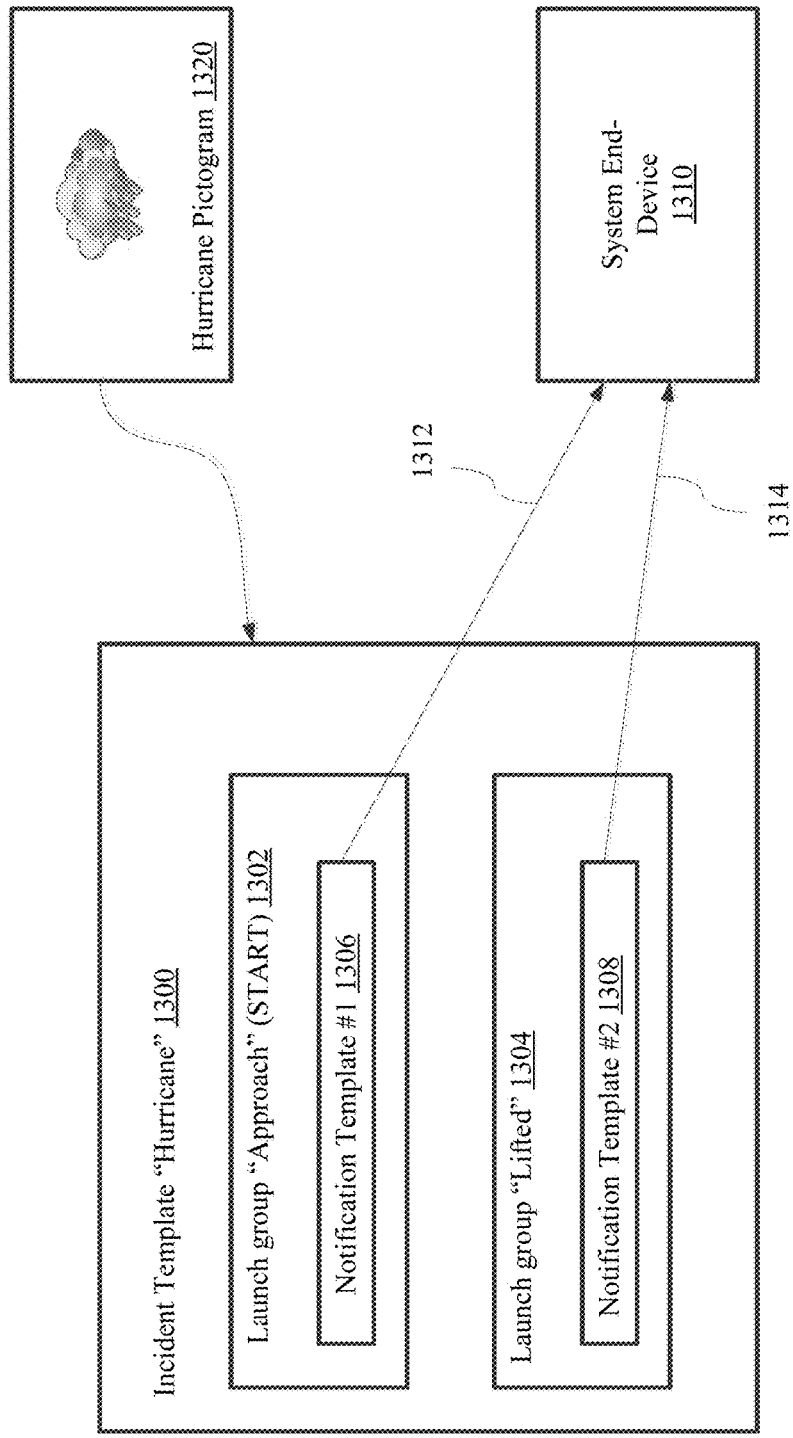
FIG. 13 is a block diagram is of an example of an implementation of the example Incident Template for a hurricane, described in relation to FIGS. 10 and 11, in accordance with the invention.

In FIG. 13, a block diagram is shown for an example of an implementation of the example Incident Template 1300 for a hurricane described in relation to FIGS. 11 and 12. The Incident Template 1300 may include a first Launch Group 1302 that indicates an approach of a hurricane and a second Launch Group that indicates that the hurricane warning has been lifted 1304. In this example, both the first Launch Group 1302 and second Launch Group 1304 may each include one Notification—notification #1 1306 and notification #2 1308, respectively. In this example, the Incident-centric MNS system may include a system end-device 1310, which may be, for example, a visual display such as a LED sign. Notification #1 1306 and notification #2 1308 may be sent by the MNS Notification Engine 314 to for display on the system end-device 1310 via signal paths 1312 and 1314, respectively. As an example of operation on the Incident-centric MNS System 200 shown in FIG. 2, the Incident Template 1300 for the hurricane may be started when the System User 304 (not shown in FIG. 13) selects a pictogram 1320 of the hurricane on the UI 305 (not shown in FIG. 13) of Terminal 302 (not shown in FIG. 13).

Figure 14:
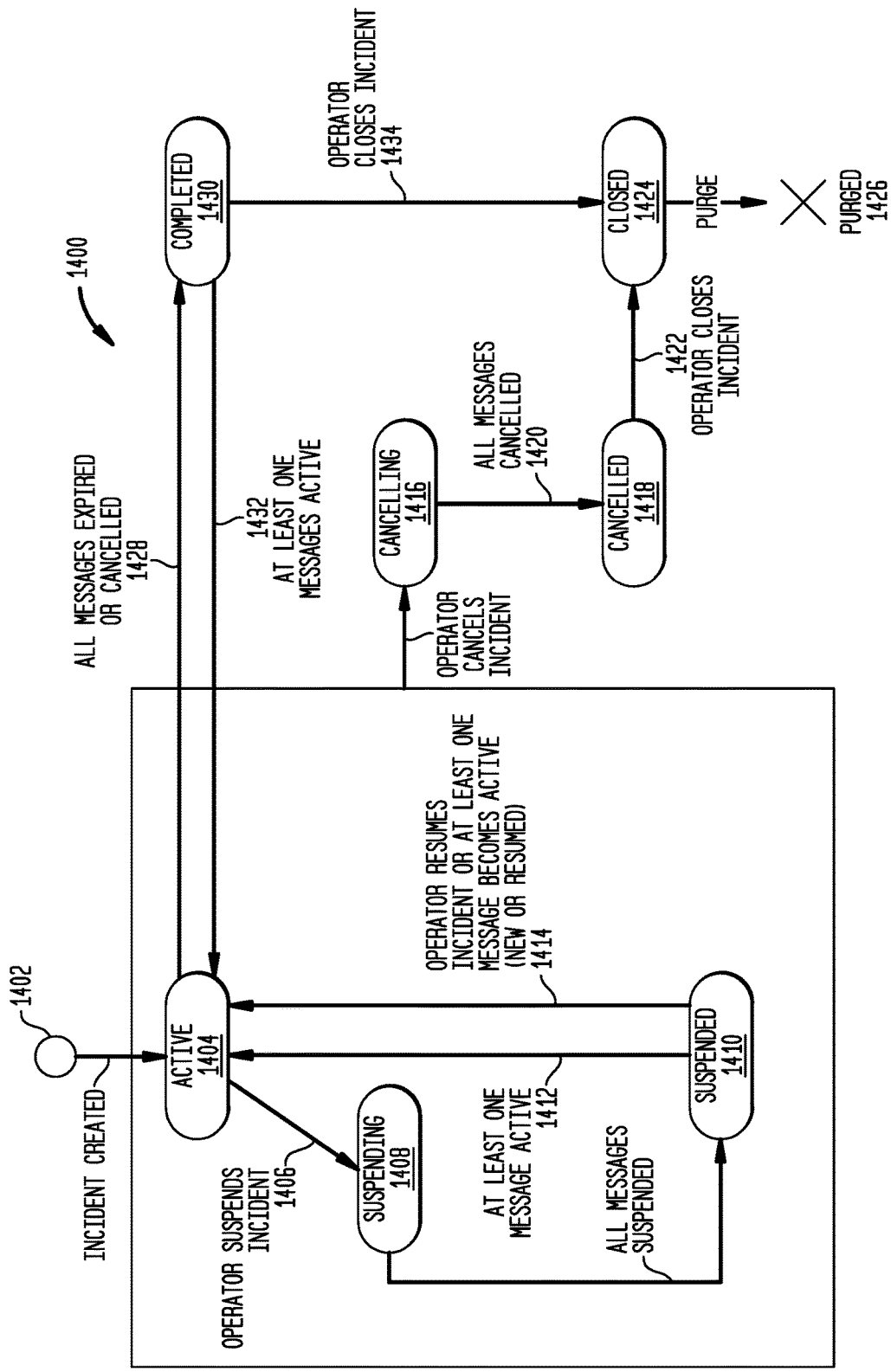
FIG. 14 is an Incident state diagram for an example of an implementation of a lifecycle of an example Incident object generated and maintained by a Mass Notification Engine of the Incident-centric MNS system based on the example Incident Template in accordance with the invention.

In FIG. 14, an MNS Incident state diagram 1400 is shown for an example of an implementation of the example Incident object generated and maintained by the MNS Notification Engine 314 in accordance with the present invention. The Incident state diagram 1400 describes the lifecycle of an Incident object within the MNS System 200. In this example, an MNS Incident (e.g., 370a in FIG. 3) is created 1402 by the MNS Notification Engine 314 and once initiated the MNS Incident is placed in an "active" state 1404 which means that at least one Notification (e.g., 372a) of the MNS Incident (e.g., 370a) has a notification state of "Active." If the System User (i.e., the Operator) uses the UI 305 to cause the MNS Notification Engine 314 to suspend an MNS Incident 1406, the state of the MNS Incident becomes a "suspending" state 1408. In the suspending state 1408, all of the Notifications associated with the respective MNS Incident are in the process of reaching a notification state "suspended" 1410 as a result of the System User suspension directive via the MNS Notification Engine 314. As an example, as a result of a System User (i.e., the System Operator) suspending the MNS Incident via UI 305 in cooperation with the MNS Notification Engine, all active and Scheduled Notifications that are Messages are subsequently suspended. However, in this example, the System 200, 900 or 1000 may be designed such that active (ongoing) Notifications that are Live Announcements cannot be suspended, and the respective MNS Incident will remain in suspending state 1408 until the MNS Notification System 314 has determined that at least all of the Live Announcements are either in pending or complete state. In the suspended state 1410, all of Notifications that are messages are suspended. Again, in this example, all the Live Announcements may be either pending or complete. If for some reason, at least one Notification message (e.g., 372a in FIG. 3) becomes active 1412, the MNS Notification Engine 314 causes the corresponding MNS Incident's state (e.g., state of 370a in FIG. 3) to become active 1404 again. Additionally, if the System User uses the UI 305 to request that the MNS Notification Engine 314 resume the MNS Incident or at least one Notification message becomes active (either because it is a new Notification message or because it is resumed) 1414, the MNS Notification Engine causes the state of the respective MNS Incident to change back to active 1404. If the System User uses the UI 305 to request the MNS Notification Engine 314 to cancel a respective MNS Incident 1416, the MNS Notification Engine 314 initiates a process to cancel or remove all of the Notifications of the respective MNS Incident in step 1420. After all the Notifications are cancelled, the MNS Notification Engine 314 changes the state of the MNS Incident to cancelled in step 1418. As a result of the System User canceling the respective MNS Incident via the MNS Notification Engine, all scheduled, active, and suspended Messages and all pending Live Announcements for the respective MNS Incident will be forced into the cancelling state 1416. However, as described before in this example, the active Live Announcements may be designed in a way that they cannot be cancelled, and the respective MNS Incident will remain in a cancelling state 1416 until at least all of the active Live Announcements are complete. The MNS Notification Engine may then enable the System User to request via UI 305 to close the MNS Incident in step 1422 and the MNS Notification Engine subsequently changes the state of the respective MNS Incident to "closed" in step 1424, after which the Incident-centric MNS System 200, 900 or 1000 may no longer allow Notifications associated with the respective MNS Incident to be launched from within this MNS Incident. The System 200, 900 or 1000 then purges 1426 the MNS Incident having the closed state in due time.

If the System User does not suspend or cancel the MNS Incident, the MNS Incident stays in state "active" 1404 until all the messages are expired or cancelled 1428 at which point the MNS Incident state changes to "completed" 1430. If at least one message becomes active 1432, the MNS Incident changes back to active 1404. Alternatively, if no messages are active, the system waits for the System User to close the MNS Incident 1434 and the MNS Incident state changes to "closed" 1424. The system then purges 1426 the MNS Incident having the closed state.

Figure 15:
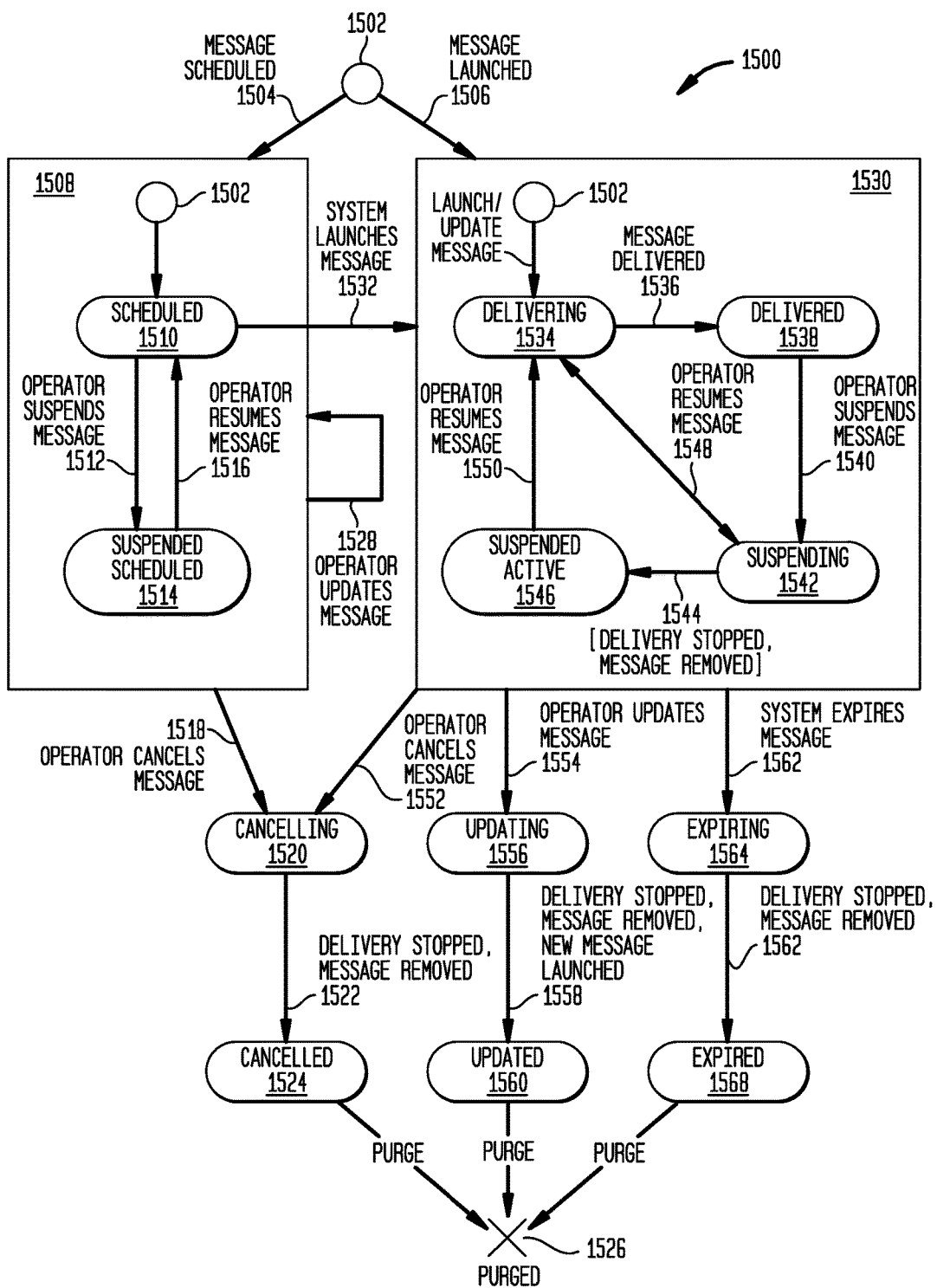
FIG. 15 is a message state diagram for an example of an implementation of a lifecycle of an example Message object generated based on the example Message Template, scheduled, launched and maintained in association with the example Incident object as processed by the MNS Notification Engine in cooperation with a MoCo Dispatcher of the Incident-centric MNS system in accordance with the invention.

In FIG. 15, a message state diagram 1500 is shown for an example of an implementation of the example Notification Message generated, scheduled, launched and maintained in association with an Incident object as processed by the MNS Notification Engine 314 in cooperation with the MoCo Dispatcher 316. The message states shown in the message state diagram 1500 describe the lifecycle of the Notification message or messages (e.g., 372*a* in FIG. 3) associated with a respective MNS Incident (e.g., 370*a* in FIG. 3). In this example, a Notification message is created in step 1502 and is either scheduled to be launched 1504 or actually launched 1506 by the MNS Notification Engine 314 in the process of instantiating or managing the respective MNS Incident.

If the Notification message is scheduled 1504, the Notification message enters into a scheduled state 1508 where the Notification message is placed in a scheduled sub-state 1510. If the System User uses the UI 305 to cause the MNS Notification Engine 314 to suspend the Notification message 1512, the Notification message is placed in a suspended scheduled sub-state 1514. If the System User uses the UI 305 to prompt the MNS Notification Engine 314 to resume the Notification message 1516, the MNS Notification Engine 314 causes the state of the Notification message to changes to scheduled sub-state 1510. If the System User uses the UI 305 to prompt the MNS Notification Engine 314 to cancel the scheduled Notification message 1518, the Notification message is placed in a cancelling state 1520 by the MNS Notification Engine 314 where the scheduled delivery of the Notification message is stopped and the Notification message is removed 1522. The MNS Notification Engine 314 subsequently causes the Notification message state to then change to cancelled 1524. The System 200, 900 or 1000 then purges 1526 the Notification message with the cancelled state in due time. If instead of cancelling the Notification message, the System User uses the UI 305 to prompt the MNS Notification Engine 314 to update the scheduled Notification message 1528, the Notification message is updated and placed again by the MNS Notification Engine 314 in the scheduled state 1510.

If instead of being scheduled, the Notification message is launched 1506 by the MNS Notification Engine 314, the Notification message is then placed by the MNS Notification Engine 314 in an active state 1530. Moreover, if instead of being cancelled or updated, the scheduled Notification message in the scheduled state 1508 is launched 1532 by the MNS Notification Engine 314, the Notification message will also be placed by the MNS Notification Engine 314 in the active state 1530. The Notification message is then placed by the MNS Notification Engine 314 in a delivering sub-state 1534 and the Notification message is subsequently delivered 1536 and placed by the MNS Notification Engine 314 in a delivered sub-state 1538. If the System User uses the UI 305 to prompt the MNS Notification Engine 314 to suspend the Notification message 1540, the Notification message state is changed by the MNS Notification Engine 314 to sub-state suspending 1542 to reflect that the delivery and presentation of the Notification message to the targeted recipient(s) has been halted temporarily 1544. The MNS Notification Engine 314 subsequently causes the Notification message state to then change to the suspended active sub-state 1546. If the System User uses the UI 305 to prompt the MNS Notification Engine 314 to resume 1548 the Notification message from the suspending sub-state 1542 or resume 1550 the Notification message from the suspended active sub-state 1546, the the MNS Notification Engine 314 changes the Notification message state back to the delivering sub-state 1534. If the System User uses the UI 305 to prompt the MNS Notification Engine 314 to cancel the Notification message 1552, the Notification message is placed in a cancelling state 1520 by the MNS Notification Engine 314 to reflect the delivery and presentation of the Notification message to the targeted recipient(s) has been halted permanently 1522. The Notification message state is then changed by the MNS Notification Engine 314 to cancelled 1524. The System 200, 900 or 1000 then purges 1526 the Notification message in due time.

If instead of cancelling the Notification message, the System User uses the UI 305 to cause the MNS Notification Engine 314 to update the Notification message 1554, the Notification message is placed by the MNS Notification Engine 314 in an updating state 1556 where delivery is stopped, the old Notification message is removed and the new Notification message with updated content is launched 1558 by the MNS Notification Engine 314 before placing the Notification message in an updated state 1560. The System 200, 900 and 1000 then purges 1526 the old Notification message in due time.

If instead the Notification message expires 1562, the Notification message is placed by the MNS Notification Engine 314 in an expiring state 1564 to reflect the delivery and presentation of the Notification message to the targeted recipient(s) is being halted permanently 1566. The Notification message is then placed by the MNS Notification Engine 314 in an expired state 1568. The System 200, 900 and 1000 then purges 1526 the Notification message with the expired state in due time.

Based on the descriptions above, the following describes a general example of operation of Incident-centric MNS System for an example MNS Incident of an approaching hurricane Emergency Event. In this example, if a hurricane is approaching a System User may select (i.e., press) an Easy Button (i.e., a pictogram on the UI 305) that has been established for this type of MNS Incident for response to this Emergency Event as described previously. Once the System User has pressed the hurricane Easy Button, the MNS Notification Engine 314 of the Incident-centric MNS System 200, 900 or 1000 creates an Incident object (e.g., 370*a* in FIG. 3) out of the MNS Incident Template "Hurricane" (e.g., 400*a* in FIG. 3) as retrieved from the MNS Incident template hierarchy (e.g., 400*a*-400*n*). In the example implementation shown in FIG. 3, this created MNS Incident object 370*a* will exist in the MNS Core Logic Module 306 and its existence will be reflected in the UI 305. However, as one of ordinary skill in the art may appreciate, the MNS Incident object 370*a* may upon creation initially exist and be stored with the UI 305 in the memory (not shown) of the System Server Station 300 or 1014. The MNS Incident object 370*a* as managed by the MNS Notification Engine may display the following information on the UI for the System User: additional instructions for the System User on emergency operating procedures, the MNS Incident progress; launch group details (with the associated notifications); and MNS Incident details. At this point, the System User may perform the following tasks: view the details of the respective MNS Incident 370*a*; select the Launch Group under which the System User desires to initiate the MNS Incident; add any other Notifications to the selected Launch Group; and view the Notification details as referenced in FIGS. 4, 5 and 6. Once the MNS Incident-centric MNS System 200, 900 or 1000 has processed all the information, it will prompt the System User to confirm initiation of the MNS Incident 370*a*. Once the System User confirms, the Incident-centric MNS System 200, 900 or 1000 will initiate the MNS Incident via the MNS Notification Engine 314. In this example, when the MNS Incident 370*a* is initiated, the MNS Incident object is packaged up and sent from the System User UI 305 to the MNS Notification Engine 314 on the System Server Station 300 or 1014. Alternatively, upon System User confirmation, the UI 305 may signal the MNS Notification Engine 314 to instantiate or generating the MNS Incident or Incident object 370*a* based on the selected MNS Incident Template (e.g., 400*a*).

Upon receiving or generating the MNS Incident object 370*a* from the UI 305, the MNS Notification Engine 314 re-establishes this Incident object, with state set to "Active." Upon scanning or processing the object, the MNS Notification Engine 314 recognizes that the START launch group is Launch Group "Approach", which has one Notification Template, #1 1306 as depicted in FIG. 13. It is appreciated that this Notification Template 1306 could have been further customized by the System User using the UI 305. In any case, the MNS Notification Engine 314 will create a Notification message object (e.g., 372*a*) out of this Notification Template 1306 and associate this Notification message object 372*a* with the respective MNS Incident object 370*a*, with the state of the Notification message object set to "Delivering," 1534 and will subsequently forward the Notification message object to the Modality Corridor Dispatcher for further processing.

Upon receiving the Notification message object 372*a* from the MNS Notification Engine, the Modality Corridor Dispatcher determines the MNS End-Point Address (e.g., the Address of MNS End-Point 380, 382, 384 or 386) and MNS Modality of each recipient in the Notification message. In this example (for ease of illustration), there is only one recipient which is an LED Sign system end-device that has one MNS End-Point (e.g., 380) and the resolved MNS End-Point Address is an IP address. The modality is specific for this LED sign, for example, "LED-SIGN."

In general, for each recipient in the Notification message, an individual Notification message object will be created. The Modality Corridor Dispatcher inspects the modality of the Notification message and searches for the appropriate Modality Corridor Handler that can and should handle the delivery of this Notification message, based on an open, configurable, business-oriented rule set. The Modality Corridor Dispatcher then forwards the Notification message object to the selected Modality Corridor Handler for delivery to the resolved MNS End-Point Address of the recipient. It is appreciated that multiple Notification messages may be batched and processed as one unit of delivery through the selected Modality Corridor Handler.

Upon receiving the Notification message object from the Modality Corridor Dispatcher, the Modality Corridor Handler uses the Delivery Path Router to find the proper set of System Intermediate Devices that should deliver the Notification message, based on a limited, configurable, and technical rule set for that corridor. Once the Notification message has traversed the delivery path on the way to the MNS End-Point, there will be a point where it leaves the corridor (and the MNS Notification Engine's scope of management), at which point the Notification message's state is changed to "Delivered."

Upon receiving the Notification message's state change, from "Delivering" to "Delivered," and given that this is the only active Notification message 372*a* in the MNS Incident 370*a*, all Notification messages of this MNS Incident 370*a* have been delivered by the MNS Notification Engine and that will be reflected on the delivery statistics on the UI for this MNS Incident.

Additionally, if the Notification message has been set to expire after a certain time, then at that point the Notification message state will be changed by the MNS Notification Engine to "Expiring," the Notification message will be removed from the LED sign, and when that has finished, it's state will be set by the MNS Notification Engine to "Expired." At this point, the MNS Notification Engine changes the state of the MNS Incident from "Active" to "Completed." The MNS Incident may move back to Active if other Notification messages associated with this MNS Incident are launched by the MNS Notification Engine as described herein.

If the hurricane is no longer a danger, the System User may use the UI 305 to navigate the MNS Incidents 370*a*-370*c* being managed by the MNS Notification Engine 314 to the Launch group "Lifted" 1304 of the selected MNS Incident 370*a* and prompt the MNS Notification Engine 314 to launch the Notification message in that group. This Notification 1308 will be delivered through the Incident-centric MNS System to the LED sign in the same way that was previously described in relation to the approach Notification 1306.

Once the Notification messages for this MNS Incident 370*a* have expired, if the System User desires to close this MNS Incident, the System User uses the UI 305 to again navigate to the respective MNS Incident object, which is now in the Completed state, and selects the close option (not shown) on the UI 305 to cause the MNS Notification Engine to close the Incident object. The MNS Notification Engine will then cause the Incident object to change state from Completed to Closed. At this point the process has ended and this MNS Incident can no longer be used. Its past history may be available via the reporting functionality of the MNS Incident-centric MNS System.

Figure 16:
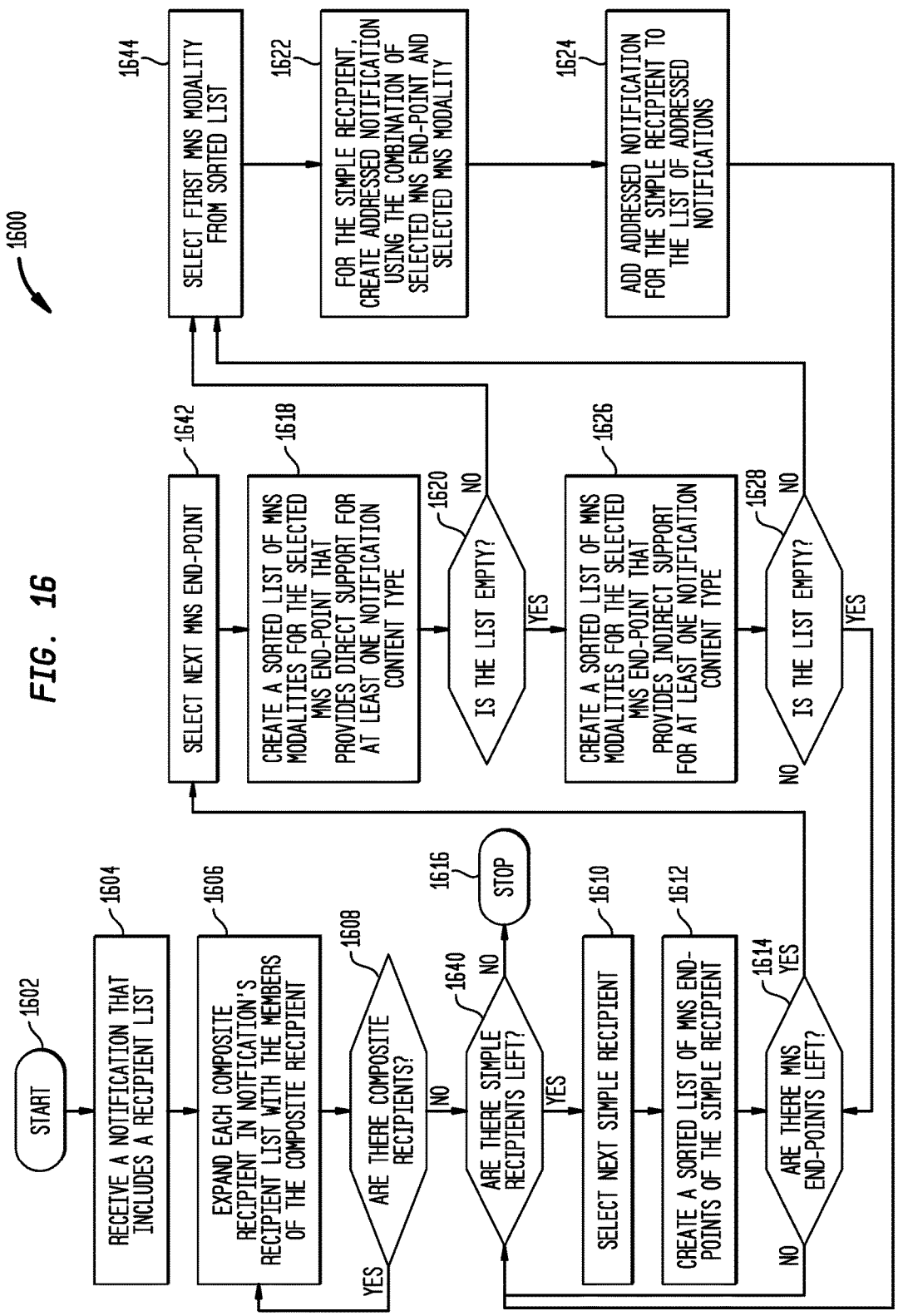
FIG. 16 is a flowchart of an example of an implementation of a process performed by the MoCo Dispatcher (of FIG. 3) in performing a resolution stage as part of delivering Notifications for the Incident-centric MNS System in accordance with the invention.
Figure 17:
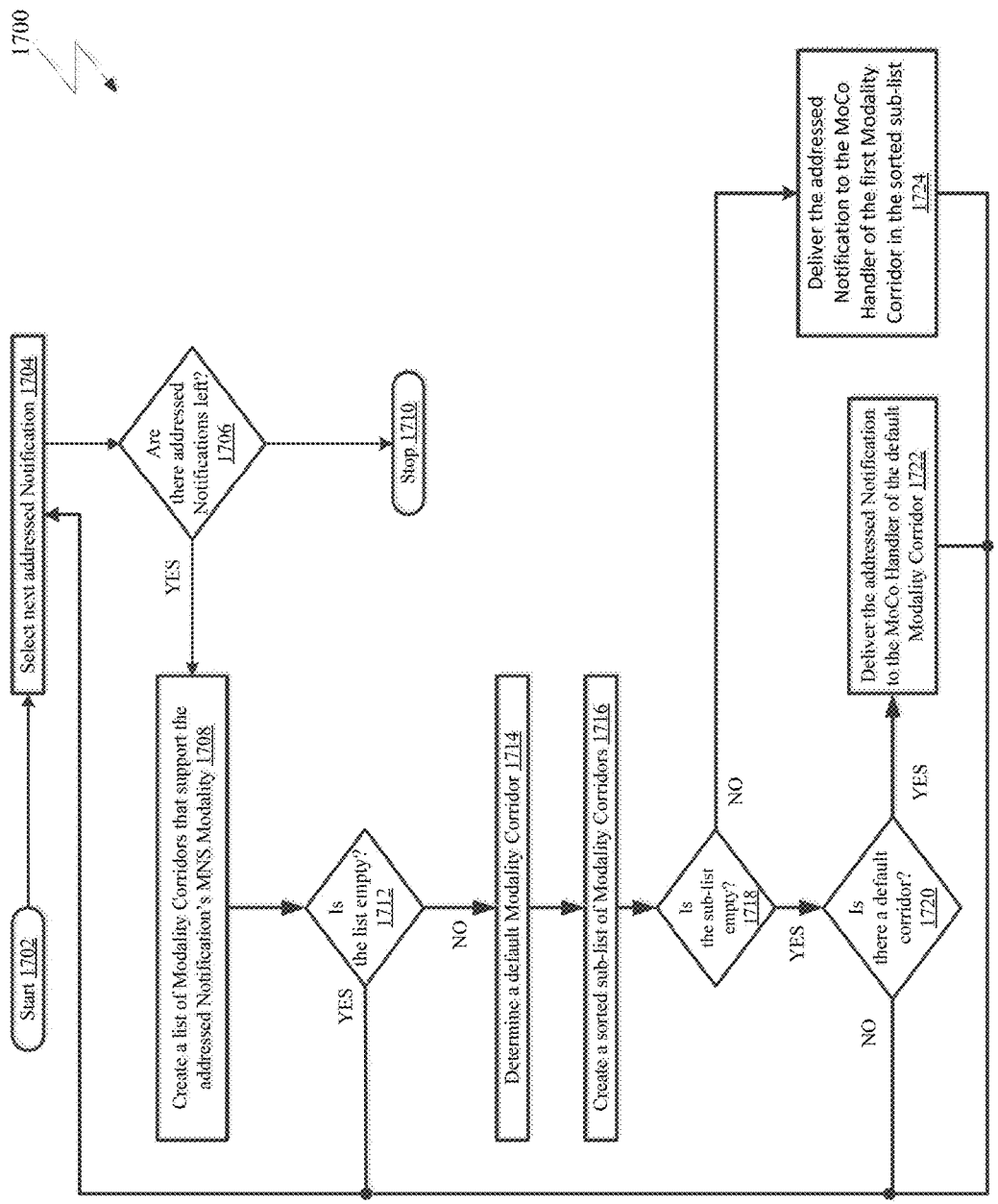
FIG. 17 is a flowchart of an example of an implementation of another process performed by the MoCo Dispatcher (of FIG. 3) in performing a dispatch stage as part of delivering Notifications for the Incident-centric MNS System in accordance with the invention.

Turning to FIGS. 16 and 17, both figures show flowcharts of the process performed by the MoCo Dispatcher 316 (of FIG. 3) in performing delivery of Notifications for the Incident-centric MNS System 200 in accordance with the invention. In general, the MoCo Dispatcher performs two stages of delivery Notifications which may be generally referred to as a resolution stage (stage 1 as shown in FIG. 16) and dispatch stage (stage 2 as shown in FIG. 17). These delivery Notifications are related to the MNS Modalities.

In this example, MNS End-Devices provide access to one or more MNS End-Points and an MNS End-Point is addressed via one MNS End-Point address. Additionally, the MNS End-Point supports one or more MNS Modalities. Examples of MNS End-Devices, MNS End-Points, MNS End-Point Addresses, and MNS Modalities are shown below in Table 1.

TABLE 1

| MNS End-Device | MNS End-Point | MNS End-Point Address | MNS Modalities |
| --- | --- | --- | --- |
| Laptop | Skype ® Account | myskype555 | "Skype MSG", "Skype Call" |
|  | Email Account | myemail555@yahoo.com | "EMAIL" |
| Home Phone Device | Phone 1 | +1 848 555 1245 | "Phone Call" |
| Business Phone Device | Phone 2 | +1 848 555 1241 | "Phone Call" |
| Smart Phone Device | Mobile Phone | +1 848 555 5432 | "Phone Call", "SMS", "MMS", |
|  | Email Account | myemail555@yahoo.com | "EMAIL" |
|  | Skype ® Account | myskype555 | "Skype MSG", "Skype Call" |
| LED Sign | LED Sign | 192.168.1.254 | "LED SIGN MSG" |

In general, an MNS Modality is the name of an agreed-upon method of delivery (agreed between the Recipient and MNS System 200, 900 or 1000) based on any of the three Notification Content Types: Audio, Text, and Multi-Media. MNS Modalities are set on a per MNS End-Point Type basis. So, in the above example, every Skype® Account has the same modalities: "Skype MSG" and "Skype Call." Generally, the MNS Notifications are targeted to MNS Recipients and the MNS Recipients 242 fall into two categories: Simple Recipients (i.e., Recipient Users and System End-Devices), and Composite Recipients (i.e., Recipient Locations and Recipient Groups). In this example, the MoCo Dispatcher 316 performs two stages for delivering Notifications.

Stage 1, referred to herein as the resolution stage, is a stage that resolves each MNS Recipient to one or more MNS End-Points and one or more MNS Modalities for each of these MNS End-Points, based on a configurable resolution rule set. During this stage, a Notification may result in one or more addressed Notifications, where an addressed Notification is a combination of Notification Content, an MNS End-Point Address, and an MNS Modality.

Stage 2, referred to herein as the dispatch stage, is a stage wherein for each addressed Notification of Stage 1, a Modality Corridor is chosen that supports its delivery, based on a configurable MoCo dispatch rule set. Once this stage is complete, the MoCo Dispatcher 316 sends the addressed Notification to the MoCo Handler of the chosen Modality Corridor, where the Modality Corridor has properties, which are available to the MoCo Dispatcher 316 for evaluating the MoCo Dispatch rules. Example of such properties include supported modalities, price per Notification message, maximum number of Notification messages, maximum content size, availability, modality corridor preference, modality corridor default, load, etc.

Turning to FIG. 16, a flowchart 1600 of the process performed by the MoCo Dispatcher 316 in performing delivery of Notifications within the resolution stage for the Incident-centric MNS System 200 is shown. In this example of the resolution stage, the input to the MoCo Dispatcher 316 is a Notification that includes a Recipient List that includes Recipients 242 that may be System End-Devices, Recipient Users (i.e., individuals and indirectly their Recipient User End-Devices), Recipient Groups, and Recipient Locations. Additionally, this Notification may also contain the content of Notification and other Notification properties. The output of the resolution stage is a list of addressed Notifications, wherein each addressed Notification includes a single MNS End-Point address and a single MNS Modality, in addition to the content of the Notification and other Notification properties. In this example, the process starts 1602 and MoCo Dispatcher 316 receives a Notification that includes a Recipient List in step 1604. In step 1606, the MoCo Dispatcher 316 expands each Composite Recipient (i.e., Recipient Group and Recipient Location) in the Recipient List of the Notification into the members of that Composite Recipient (e.g., Recipient Location "Building 5" will be replaced with the Recipient Users and System End-Devices of "Building 5"). The MoCo Dispatcher 316 determines, in decision step 1608, that there are still Composite Recipients in the Recipient List of the Notification, the process returns to step 1606 and those Composite Recipients are also expanded into the members of those corresponding Composite Recipients. If instead, there are no more Composite Recipients, the process continues to step 1640 where the MoCo Dispatcher 316 determines that there are (still) Simple Recipients to be processed, and the process continues with step 1610. If instead there are no more Simple Recipients left to be processed, the Resolution process stops at step 1616.

If instead, there are more Simple Recipients, the process continues to step 1610, where Recipient List of the Notification only contains Simple Recipients and each Simple Recipient contains a list of one or more MNS End-Points (e.g., three end-points). In this example, each MNS End-point refers to an MNS End-Point Type (e.g., a mobile phone, email account, Skype® account, etc.) and includes an MNS End-Point address (e.g., +8485551245, myemail555@domain.com, myskype555, etc.). In this example, each MNS End-Point Type supports one or more MNS Modalities (e.g., type mobile phone supports modalities "phone call", "SMS", and "MMS", type "email account" supports modality "email", and type "Skype® account" supports modalities "Skype MSG" and "Skype Call").

Furthermore, in this example, the MNS End-Points of a Simple Recipient may be ranked, such as, for example, ranked according to the Recipient's preference and other properties (e.g., a Simple Recipient may prefer "Skype® account" over "mobile phone" over "email account"), and the MNS Modalities of each MNS End-Point may be also ranked according to the Recipient's preference (e.g., for "mobile phone" the Simple Recipient may prefer "SMS" over "phone call" over "MMS").

And finally, for each MNS Modality there may be a Content Compatibility Matrix that explains how MNS handles the various Notification Content Types for that modality. For each cell in this matrix, there may be three possible values: 1) "Direct Support," where the MNS Modality supports the MNS Content Type (e.g., audio content can be delivered via the "phone call" modality); 2) "Indirect Support," where the MNS Modality indirectly supports the MNS Content Type by converting it to another content type (e.g., text content can be converted to audio content for delivery via the "phone call" modality); and "Not Supported," where the MNS Modality does not support the MNS Content Type (e.g., multi-media content (video) may NOT be delivered via the "phone call" modality). In step 1610, the Recipient List only includes Simple Recipients and the process continues where, in step 1612, for the selected Simple Recipient in step 1610, a sorted list of MNS End-Points of the Simple Recipient is created based on a ranking method that includes the preferences of the Simple Recipient. The process then continues with step 1614 to process each MNS End-Point in sorted order, and where the process will continue with step 1642 if there are still MNS End-Points left to be processed, otherwise the process returns to step 1640 for the processing of the next Simple Recipient. Having determined that there are MNS End-Points left to be processed in step 1614, the process continues with step 1642 by selecting the next MNS End-Point from the sorted list of step 1612.

In step 1618, a sorted list of Direct Support MNS Modalities is created for the MNS End-Point based on a ranking method that includes, for example, the preferences of the Simple Recipient, and where the Direct Support for the MNS Content Type of the Notification is as per the content compatibility matrix. The process then determines, in decision step 1620, if the sorted list is not empty. If the sorted list is not empty, the process continues to step 1644 where the selected MNS Modality for the Simple Recipient is set to the first modality in the sorted list and the process continues to step 1622. In step 1622, an addressed Notification is created for the Simple Recipient, using the selected MNS End-Point and the selected MNS Modality. The process then continues to step 1624. In step 1624, the address Notification as created in step 1622 for the Simple Recipient is added to the list of the addressed Notifications. The process then repeats by returning to step 1640.

If instead, the sorted list is empty, the process continues to step 1626. In step 1626, a sorted list of Indirect Support MNS Modalities for the MNS End-Point is created based on a ranking method that includes the preferences of the Simple Recipient, and where the Indirect Support. The process then determines, in decision step 1628, if the sorted list is not empty.

If the sorted list is not empty, the process continues to step 1644 where the selected MNS Modality for the Simple Recipient is set to the first modality in the sorted list and the process continues to step 1622. In step 1622, an addressed Notification is created for the Simple Recipient, using the selected MNS End-Point and the selected MNS Modality. The process then continues to step 1624. In step 1624, the addressed Notification as created in step 1622 for the Simple Recipient is added to the list of the addressed Notifications. The process then repeats by returning to step 1640.

If instead, the sorted list is empty, the process returns to step 1614 where the next MNS End-Point in the list of the Simple Recipient is selected.

Table 2 shows an example of a Content Compatibility Matrix. It is appreciated that Indirect Support (1) may be indirect support though a Text-to-Speech ("TTS") engine (e.g., the text content of a message will be run through a TTS engine and the resulting audio file will be delivered to the end-point by calling the phone number and playing the audio content).

TABLE 2

| Notification Content Type | MNS Modalities | | | |
|---|---|---|---|---|
| | "Phone Call" | "EMAIL" | "SMS" | Etc. |
| Text | Indirect Support (1) | Direct Support | Direct Support | Etc. |
| Audio | Direct Support | No Support | No Support | Etc. |
| MM | No Support | No Support | No Support | Etc. |

Turning now to FIG. 17, a flowchart 1700 of the process performed by the MoCo Dispatcher 316 in performing delivery of Notifications within the dispatch stage for the Incident-centric MNS System 200 is shown. In this example, the dispatch stage may have six inputs that include: 1) a list of addressed Notifications, where each addressed Notification contains a single MNS End-Point address and a single MNS Modality, in addition to the content and other notification properties; 2) Notification properties that include Notification priority, number of notifications, content size, etc.; 3) MNS End-Point address properties (e.g., email domain, local vs. long-distance telephone number), etc.; 4) the properties of each Modality Corridor, such as, for example, supported modalities, price per message, maximum number messages, maximum content size, current availability, current load, preference ranking, designated default, etc.; 5) environmental properties such as time of day, day of week, etc.; and 6) one dispatch rule for each Modality Corridor that uses the above properties and produces a Boolean result, as well as one ranking rule for each Modality corridor that uses the above properties and produces a ranking number. In general, the MoCo Dispatcher 316 attempts to send each addressed Notification to the appropriate Modality Corridor for delivery processing based on these six inputs.

The process starts in step 1702 with a list of addressed Notifications from stage 1. The MoCo Dispatcher 316 then proceeds to step 1704 where the next addressed Notification is retrieved from the list. The process then continues with decision step 1706, where the process will continue with step 1708 if there are still addressed Notifications left to be processed, otherwise the process stops at step 1710. Continuing the process with the retrieved address Notification, in step 1708 a list of Modality Corridors that support the MNS Modality of the addressed Notification is created. The MoCo Dispatcher 316 then determines, in decision step 1712, if the list of Modality Corridors is empty. If the list of Modality Corridors is empty, the addressed Notification is undeliverable for this MNS Modality and the process repeats to step 1704 where the next addressed Notification is selected.

If instead, the list of Modality Corridors is not empty, the process continues to step 1714 where MoCo Dispatcher 316 determines a default Modality Corridor in the list of Modality Corridors based on the properties of the Modality Corridors (e.g., "designated default" property). In step 1716, a sorted sub-list of Modality Corridors is created, out of the list of Modality Corridors, whose Modality Corridor dispatch rule is evaluated to "TRUE." This list is sorted based on the numerical evaluation results of the ranking rules of those Modality Corridors whose dispatch rules evaluated to "TRUE." The process then determines, in decision step 1718, if the sub-list of Modality Corridors is empty. If the sub-list of Modality Corridors is empty, the process continues to decision step 1720. In decision step 1720, if there is no default Modality Corridor determined then the addressed Notification is undeliverable for this MNS Modality and the process repeats to step 1704 where the next addressed Notification is selected.

If instead, there is a default Modality Corridor determined, the process continues to step 1722 where the MoCo Dispatcher 316 delivers the address Notification to the MoCo Handler of the default Modality Corridor and then process then repeats to step 1704 where the next address Notification is selected.

If instead, the sub-list of Modality Corridors is not empty, in decision step 1718, the process continues to step 1724 to deliver the addressed Notification to the MoCo Handler of the first Modality Corridor in the sorted sub-list. The process then repeats to step 1704 where the next address Notification is selected.

It is appreciated that after the addressed Notification has reached the MoCo Handler, the MNS Modality and other Notification and Recipient properties may still play a role during the process of finding a delivery path to the MNS End-Point within the Modality Corridor.

Although the previous description only illustrates particular examples of various implementations, the invention is not limited to the foregoing illustrative examples. A person skilled in the art is aware that the invention as defined by the appended claims can be applied in various further implementations and modifications. In particular, a combination of the various features of the described implementations is possible, as far as these features are not in contradiction with each other. Accordingly, the foregoing description of implementations has been presented for purposes of illustration and description. It is not exhaustive and does not limit the claimed inventions to the precise form disclosed. Modifications and variations are possible in light of the above description or may be acquired from practicing the invention. The claims and their equivalents define the scope of the invention.

What is claimed is:

1. A Mass Notification System ("MNS") Notification Engine for use in Incident-centric Mass Notification System ("Incident-centric MNS system"), the MNS Notification Engine comprising:
   logic configured to manage a plurality of MNS Incidents and a plurality of Notifications, wherein the logic configured as an incident template includes logic configured as an incident template content,
   wherein the logic configured as incident template content includes at least one set of logic configured as a launch group,
   wherein the at least one set of logic configured as a launch group includes logic configured as a notification template and the logic configured as a notification template includes data structures configured to hold pre-configured information about the plurality of Notifications and the logic configured as a notification template is included in logic configured as a Notification Template Hierarchy; and
   a user interface ("UI") that allows an MNS User to interface with the MNS Notification Engine.

2. The MNS Notification Engine of claim 1, wherein the MNS User is a System Operator, wherein the System Operator is a System User for operating the Incident-centric MNS system during an Emergency Event.

3. The MNS Notification Engine of claim 1, wherein the logic configured as a notification template includes logic configured as a Message Template, logic configured as a Live Announcement Template, or both.

4. The MNS Notification Engine of claim 3, wherein the logic configured as a Message Template includes a data structure configured to hold pre-configured details of a Message and wherein the logic configured as a Live Announcement Template includes a data structure configured to hold pre-configured details of a Live Announcement.

5. The MNS Notification Engine of claim 4,
   wherein an MNS Incident, of the plurality of MNS Incidents, includes a plurality of MNS Incident states,
   wherein the logic configured as a launch group includes a plurality of Notification Templates, and
   wherein the launch group is configured to launch the plurality of Notification Templates simultaneously during an MNS Incident state of the plurality of MNS Incident states.

6. The MNS Notification Engine of claim 5, wherein the plurality of MNS Incident states includes states selected from the group consisting of an active state, suspended state, suspending state, cancelled state, cancelling state, all-clear state, completed state, and closed state.

7. The MNS Notification Engine of claim 6,
   wherein the UI includes a plurality of graphical pictograms,
   wherein each graphical pictogram represents an Emergency Event from a plurality of Emergency Events,
   wherein the MNS User is a System Operator,
   wherein the System Operator is a System User for operating the Incident-centric MNS system during an Emergency Event, and
   wherein the UI is configured to allow a System Operator to quickly initiate an MNS Incident and launch a notification.

* * * * *